United States Patent [19]

Bare

[11] Patent Number: 4,552,883
[45] Date of Patent: Nov. 12, 1985

[54] PYRAZOLO[3,4-b]PYRIDINE CARBOXYLIC ACID ESTERS AND THEIR PHARMACEUTICAL USE

[75] Inventor: Thomas M. Bare, West Chester, Pa.

[73] Assignee: ICI Americas Inc., Wilmington, Del.

[21] Appl. No.: 496,259

[22] Filed: May 19, 1983

[30] Foreign Application Priority Data

Jun. 15, 1982 [GB] United Kingdom ............... 8217258

[51] Int. Cl.$^4$ ................... A61K 31/44; C07D 471/04
[52] U.S. Cl. ................................... 514/303; 546/120
[58] Field of Search .................. 546/120; 424/256; 514/303

[56] References Cited

U.S. PATENT DOCUMENTS

| 3,755,340 | 8/1973 | Hoehn et al. | 546/120 |
| 3,849,411 | 11/1974 | Hoehn et al. | 546/120 |
| 4,364,948 | 12/1982 | Heald et al. | 546/120 |

FOREIGN PATENT DOCUMENTS

1402172 8/1975 United Kingdom .

OTHER PUBLICATIONS

Puar et al., J. of Pharm. Sciences, 67(6), Jun. 1978, pp. 850–853.

Primary Examiner—Henry R. Jiles
Assistant Examiner—Bernard I. Dentz
Attorney, Agent, or Firm—Rosemary M. Miano

[57] ABSTRACT

Compounds of the formula (I):

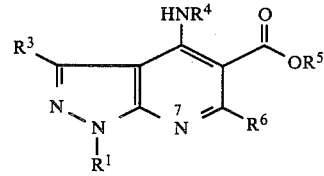

wherein $R^1$, $R^3$, $R^4$, $R^5$ and $R^6$ have defined values and the N-oxides at the 7-position of the pyrazolo[3,4-b]pyridine ring system and the pharmaceutically-acceptable acid-addition salts thereof, processes for their preparation and use, pharmaceutical compositions, and intermediates for preparing said compounds of the formula (I). The compounds of formula (I) are central nervous system depressants, for example anxiolytic agents.

9 Claims, No Drawings

PYRAZOLO[3,4-b]PYRIDINE CARBOXYLIC ACID ESTERS AND THEIR PHARMACEUTICAL USE

The invention comprises certain pyrazolo[3,4-b]-pyridines, their use as central nervous system depressants, methods for their preparation, pharmaceutical compositions and intermediates used in their preparation. Prior chemical structures having the pyrazolo[3,4-b]pyridine ring system are found in U.S. Pat. No. 3,755,340.

SUMMARY OF THE INVENTION

The invention comprises certain novel compounds which have been found to possess considerable pharmaceutical activity as anxiety-reducing agents in animals such as in man. Compared to known anxiolytic agents such as diazepam, invention compounds show reduced side effects of sedation and potentiation of the effects of ethyl alcohol. The invention also encompasses pharmaceutical compositions to be given to a subject in need of an anxiety-reducing medication, and intermediates used in the preparation of the active compounds of the invention.

DETAILED DESCRIPTION OF THE INVENTION

The invention compounds are of the formula (I):

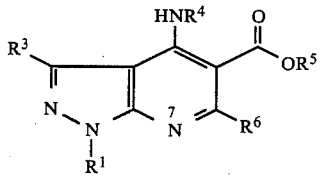

wherein
$R^1$ is alkyl, cycloalkyl, cycloalkylalkyl, alkenyl, alkynyl, arylalkyl, alkyl into which is inserted a divalent moiety selected from the group consisting of oxygen, sulfur, sulfinyl or sulfonyl, or alkyl substituted by a hydroxy, amino, alkylamino, dialkylamino, cyano, oxo, ketal, hemiketal, acetal or hemiacetal group or by one or more halogen atoms;
$R^3$ is hydrogen or alkyl;
$R^4$ is hydrogen, alkyl, hydroxy-substituted alkyl or oxo-substituted alkyl;
$R^5$ is alkenyl, alkynyl, hydroxyalkyl, cycloalkyl, cycloalkylalkyl, alkoxyalkyl, haloalkyl, haloalkenyl, arylalkyl, arylalkenyl or aryl; and
$R^6$ is hydrogen or alkyl,
and the N-oxides at the 7-position of the pyrazolo[3,4-b]-pyridine ring system, and the pharmaceutically-acceptable acid-addition salts thereof.

$R^1$, in particular, is a straight or branched chain alkyl of 1 to 10 carbons, or particularly 3 to 7 carbons, e.g., n-pentyl, 1-, 2- or 3-methyl-n-butyl, 1- or 2-ethyl-n-butyl, n-hexyl, 1-, 2-, 3- or 4-methyl-n-pentyl, n-heptyl or n-octyl; a cycloalkyl of 3 to 8 carbons, more particularly 5 to 7 carbons, e.g., cyclohexyl; a cycloalkylalkyl of 4 to 12 carbons, e.g., cyclopropylethyl; an alkenyl or alkynyl of 3 to 10 carbons, such as from 3 to 7 carbons, e.g., allyl, 3-butenyl, 2-methyl-2-propenyl, propargyl, 5-hexynyl, 3-butynyl, 3- or 4-pentynyl, 2-, 3- or 4-pentenyl, 3-methyl-2- or 3-butenyl, allenyl, 1,3-butadienyl or 2,4-pentadienyl; arylalkyl of 7 to 12 carbons, e.g., benzyl; straight or branched chain alkyl of 1 to 10 carbons, particularly 3 to 7 carbons, into the backbone of which has been inserted an oxygen, sulfur, sulfinyl or sulfonyl divalent moiety with examples being 3-methoxypropyl, 2-ethoxyethyl, 2-methoxyethyl, 2-(ethylthio)ethyl, ethylsulfinylethyl (the S-oxide of ethylthioethyl), ethylsulfonylethyl, 3-ethoxypropyl or 4-methoxybutyl; or straight or branched chain alkyl of 1 to 10 carbons, particularly 3 to 7 carbons, substituted by a hydroxy, amino, 1 to 6 carbon alkylamino, 2 to 12 carbon dialkylamino, cyano, oxo, ketal, hemiketal, acetal, or hemiacetal group or by one or more of chloro, bromo, iodo or fluoro, particularly fluoro, the alkyl group or groups of the ketal, hemiketal, acetal or hemiacetal groups having 1 to 6 carbons each, which may be linked to form a dioxo ring, e.g., a 1,3-dioxolane ring, with specific examples of the entire group being 4-oxo-n-pentyl, 4-hydroxy-n-pentyl, 4-(1,2-ethylenedioxy)-n-pentyl, 4,4,4-trifluoro-n-butyl, 5,5,5-trifluoro-n-pentyl, 4-cyano-n-butyl or 3-cyano-n-propyl. Preferably, the double or triple bond, if any, of $R^1$ is not on the carbon directly attached to nitrogen of the pyrazole ring. Further, the carbon of $R^1$ attached directly to the nitrogen of the pyrazole ring preferably has at least one hydrogen attached to it, e.g., it is a —$CH_2$— group.

$R^3$, in particular, is a hydrogen atom or a straight or branched chain lower alkyl of 1 to 6 carbons, e.g., methyl.

$R^4$, in particular, is hydrogen; a straight or branched chain alkyl of 1 to 10 carbons, more particularly 1 to 6 carbons such as n-butyl; or a hydroxy- or oxo-substituted alkyl, such as an aldehydo- or keto-substituted alkyl, of 1 to 10 carbons, more particularly 1 to 6 carbons such as 3-hydroxy-n-butyl, 4-oxo-n-butyl or 3-oxo-n-butyl.

$R^5$, in particular, is straight or branched chain alkenyl of 3 to 7 carbons such as allyl, 1- or 2-methyl-2-propenyl, 1-, 2- or 3-methyl-2-butenyl, 1-, 2-, 3- or 4-methyl-2-pentenyl, 2- or 3-butenyl, 2,4-pentadienyl or 1-, 2-, 3- or 4-methyl-2,4-pentadienyl, the double bond of the alkenyl preferably not being located on the carbon directly attached to the ester oxygen; an alkynyl of 3 to 7 carbons such as 2-propargyl, 2- or 3-butynyl, 1-methyl-2-butynyl, 1- or 2-methyl-3-butynyl or 1-ethyl-2 or 3-butynyl, the triple bond of the alkynyl preferably not being located on the carbon directly attached to the ester oxygen; hydroxy(straight or branched chain)alkyl of 1 to 7 carbons such as 2- or 3-hydroxyethyl or 2- or 3-hydroxy-2-methylbutyl, the hydroxy not being located on the carbon directly attached to the ester oxygen; cycloalkyl of 3 to 7 carbons such as cyclopropyl or cyclohexyl; cycloalkylalkyl of 4 to 10 carbons such as cyclopropylmethyl, cyclobutylmethyl or cyclohexylethyl; alkoxy(straight or branched chain)alkyl of 2 to 10 carbons such as methoxymethyl, 2-methoxyethyl, 1-, 2-, 3- or 4-methoxybutyl or 2-, 3- or 4-methoxy-2-methylbutyl, the alkoxy moiety preferably not being located on the carbon directly attached to the ester oxygen; chloro-, bromo-, fluoro- or iodo(straight or branched)alkyl of 2 to 7 carbons such as 2-chloroethyl, 2- or 3-chloropropyl, 2,2-, 3,3- or 2,3-dichloropropyl or 2,2,2-trifluoroethyl, a halogen preferably not being on a carbon directly attached to the ester oxygen; chloro-, bromo-, fluoro- or iodo(straight or branched chain)alkenyl of 3 to 7 carbons such as 2- or 3-chloro-2-propenyl or 2- or 3-bromo-1-methyl-2-butenyl, a halogen or the double bond of the alkenyl preferably not being located on the carbon directly attached to the ester oxygen;

aryl(straight or branched chain)alkyl of 6 to 10 carbons in the aryl portion and 1 to 7 carbons in the alkyl portion such as benzyl, phenethyl or phenyl-2-methylethyl, said aryl including substituted aryl such as aryl substituted by halogen, alkoxy, alkyl or haloalkyl; aryl(-straight or branched chain)alkenyl of 6 to 10 carbons in the aryl portion and 3 to 7 carbons in the alkenyl portion such as 1-, 2- or 3-phenyl-2-propenyl or 1-methyl-1-, 2- or 3-phenyl-2-propenyl, the double bond of the alkenyl portion preferably not being located on the carbon directly attached to the ester oxygen; or aryl such as phenyl.

$R^6$, in particular, is hydrogen or straight or branched chain alkyl of 1 to 8 carbons such as methyl, ethyl, n-propyl, iso-propyl or n-butyl.

The pharmaceutically acceptable salts of the compounds of formula (I) are, for example, physiologically acceptable acid-addition salts such as mineral acid salts, e.g., hydrohalides, especially hydrochlorides and hydrobromides, sulfates, nitrates and phosphates.

Compounds of formula (I) and intermediates therefor may exist in the form of optical isomers, e.g., where $R^1$, $R^3$, $R^4$, $R^5$ or $R^6$ is an asymmetric alkyl or alkenyl group such as 1-methylpropyl or 1-methyl-2-propenyl, or geometric isomers, e.g., the cis and trans alkenyl groups of 2-butenyl for $R^5$. The present invention comprises all such optical and geometric isomers which exhibit the above-mentioned biological activity.

One embodiment of the invention consists of compounds of the formula (I)
wherein
$R^1$ is (3-7C)alkyl, cycloalkylalkyl of not more than 7 carbons, (3-7C)alkenyl, (3-7C)alkynyl or phenyl-(1-3C)alkyl, or a (3-7C)alkyl into which is inserted a divalent moiety selected from oxygen, sulfur, sulfinyl and sulfonyl, or a (3-7C)alkyl bearing a hydroxy, cyano, oxo, ketal or trifluoromethyl substituent;
$R^3$ is hydrogen;
$R^4$ is hydrogen;
$R^5$ is (3-7C)alkenyl, (3-7C)alkynyl, cycloalkylalkyl or alkoxyalkyl of not more than 7 carbons in total, halo-(3-7C)alkenyl, phenyl-(1-3C)alkyl, phenyl-(3-7C)alkenyl or phenyl; and
$R^6$ is hydrogen or (1-3C)alkyl;
and pharmaceuticallys-acceptable acid-addition salts thereof.

Preferred compounds of the formula (I) are 4-amino-6-methyl-1-pentyl-1H-pyrazolo[3,4-b]pyridine-5-carboxylic acid cyclopropylmethyl ester, 4amino-1-(4-cyanobutyl)-6-methyl-1H-pyrazolo[3,4-b]pyridine-5-carboxylic acid allyl ester and 4amino-6-methyl-1-(4-oxo-n-pentyl)-1H-pyrazolo[3,4-b]pyridine-5-carboxylic acid allyl ester and pharmaceutically-acceptable acid-addition salts thereof.

Particularly preferred compounds of the formula (I) are 4-amino-6-methyl-1-(4-pentynyl)-1H-pyrazolo[3,4-b]-pyridine-5-carboxylic acid allyl ester and pharmaceutically-acceptable salts thereof.

The compounds of the invention may be prepared by routes analogous to those described in U.S. Pat. No. 3,755,340 and more specifically as follows, the values of the various substituents being as described above for formula (I) unless otherwise indicated. An aminopyrazole of the following formula (II):

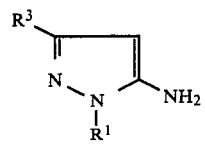

is reacted, e.g., at a temperature of about 110° to 130° C. in the presence of poly-phosphoric acid, with an alkyl-carbonyl malonic acid diester of the following formula (III):

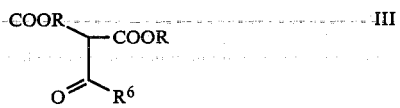

wherein R is alkyl such as lower alkyl, e.g., ethyl, to yield the intermediate of the following formula (IV):

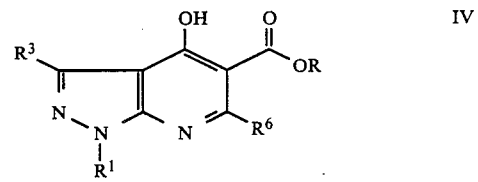

The starting material of formula (II) may be prepared as described in U.S. Pat. Nos. 3,414,580 and 3,755,340, by ring closure of an aldehyde or ketone hydrazone of the formula $R^{10}C=N-NH-CHR^3-CH_2CN$, wherein $R^{10}$ is the portion of $R^1$ other than the carbon which is directly attached to the nitrogen atom, e.g., if $R^1$ is n-pentyl, $R^{10}$ would be hydrogen and n-butyl; if $R^1$ is isopropyl, $R^{10}$ would be two methyl groups; and if $R^1$ is cyclohexyl, $R^{10}$ would be pentylene. The starting material of formula (III) may be prepared by methods generally described in Organic Synthesis, Coll. Vol. IV pages 285–288 (1963). For example, compounds of formula (III) such as acetomalonic acid diethyl ester may be prepared by the reaction of an alkane acid chloride, e.g., acetyl chloride, with the anion of a dialkyl ester of malonic acid. In preparing compounds of formula (IV) wherein $R^6$ is hydrogen, the amino-pyrazole of formula (II) may be reacted at about 80° to 150° C. with an enol or enol ether of the compound of formula (III), i.e., of the formula $(ROOC)_2C=CHOH$ or $(ROOC)_2C=CHOR$ wherein each of the R groups are independently alkyl. The reaction product is an intermediate open chain enamine of the following formula (V):

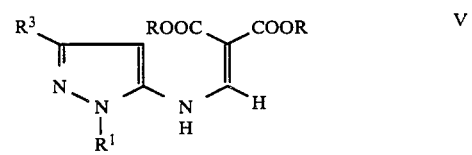

which may be then cyclized to the compound of formula (IV) wherein $R^6$ is hydrogen by heating at about 180° to 280° C. under an inert atmosphere.

The compound of formula (IV) may then be converted to a halo compound of the following formula (VI):

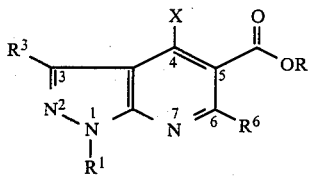

wherein X is a halogen such as chloro or bromo by reaction of (IV) with a chlorinating or brominating agent such as phosphorus oxychloride. If the desired compound of formula (I) is the N-oxide at the 7 position, the compound of formula (VI) is reacted with a peracid such as trifluoroperacetic acid or m-chloroperoxy-benzoic acid at about 0° to 100° C. in an inert solvent such as acetic acid or methylene chloride to yield the 7-position N-oxide derivative of the compound of formula (VI) which may be carried through the following sequence of reactions wherein the 7-position nitrogen is an N-oxide leading to the compound of formula (I).

The compound of formula (VI) may then be reacted with an amine of the formula $H_2NR^4$ at a temperature of about 25° to 150° C. in an organic solvent such as ethanol or toluene to yield the compound of the following formula (VII):

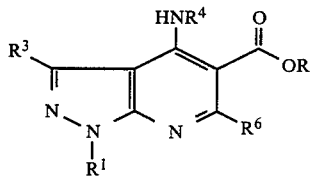

which is then hydrolyzed to the corresponding acid of the following formula (VIII):

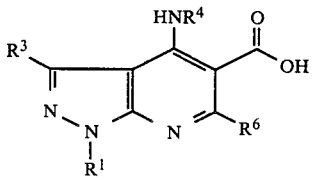

by acid or base hydrolysis, e.g., with an alkali hydroxide such as sodium hydroxide, in an aqueous solution at a temperature of about 30° to 100° C. The acid of formula (VIII) is then esterified with the appropriate compound of formula $LG—R^5$ wherein LG is a leaving group such as p-toluene sulfonate, hydroxy or a halogen, e.g., bromo, in an organic solvent such as dimethylformamide at about 0° to 80° C., preferably in the presence of a base such as potassium carbonate. A catalyst containing a good leaving group may be added, e.g., if LG is chloro, the addition of a small amount of potassium iodide will promote the reaction. The esterification may take place in two steps such as by first preparing the acid halide of the carboxylic acid of formula (VIII) followed by reaction with the alcohol $HO—R^5$.

Further, it can be seen from the above that the sequence of reactions of formula (IV) to (VI) to (VII) to (VIII) to (I), with or without the two stage esterification of the compound of formula (VIII), can be modified to achieve the same result. The sequence converts an 4—OH—5—COOR compound to a 4—NH-$R^4$—5—$COOR^5$ compound and the same result can be achieved by varying the reaction order, e.g., the ester of formula (IV) may be saponified to the corresponding 4—hydroxy—5—COOH which is then halogenated to the 4-halo-5-acid halide which is then esterified to the 4—halo—5—$COOR^5$ compound which is then reacted with $H_2NR^4$ to produce the compound of formula (I). A third synthesis method employing a sequence modification is the saponification of the 4—halo—5—COOR compound of formula (VI) to yield the corresponding 4—halo—5—COOH which may then either be halogenated to the above-described 4-halo-5-acid halide or directly esterified to the above-described 4—halo—5—$COOR^5$ compound all under conditions as previously described for the corresponding hydrolysis or saponification, halogenation and esterification. In addition, the hydrolysis and reesterification of the 5-position —COOR group in formula (VI) may be avoided by utilizing as a starting material to be reacted with the aminopyrazole of formula (II), a compound corresponding to that of formula (III) wherein R is the desired value of $R^5$.

Although the synthesis sequences described above provide the $R^1$ group at an early stage of synthesis, i.e., use of an aldehyde of the formula $R^{10}$—CHO, it is possible to provide the $R^1$ group at a later stage by converting a compound of the formula (IV) to the 4-alkoxy derivative, i.e., formula (VI) wherein the X group is alkoxy of 1 to 6 carbons, followed by removal of the $R^1$ group, particularly if $R^1$ is alkyl, with replacement by an H atom to produce a compound of the following formula (IX):

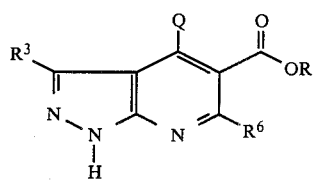

where Q is alkoxy. The reaction of (IV) to yield the alkoxy derivative is conducted at about room temperature to 100° C. with an alkyl iodide under basic conditions. The subsequent removal of $R^1$ is conducted with N-bromosuccinimide in a solvent such as $CCl_4$ under reflux. The reaction is preferably illuminated with a sunlamp, followed by aqueous hydrolysis. The compound of formula (IX) where Q is alkoxy may then be reacted with $H_2NR^4$ to yield (IX) where Q is $HNR^4$ followed by reaction with a compound of the formula $R^1$—Cl, $R^1$—I or $R^1$—Br to give compound (VII). In the alternative, the order of these two reactions may be reversed, i.e., reacting (IX) where Q is alkoxy with $R^1$—Cl, $R^1$—I or $R^1$—Br to yield (VI) where X is alkoxy followed by reaction with $H_2NR^4$ to yield (VII). The conversion of the 4-position alkoxy to $HNR^4$ in either alternative method may be conducted at room temperature to 200° C. in an apparatus such as a stainless steel pressure vessel if the required $H_2NR^4$ compound is a gas at the reaction temperature. The reaction may be conducted neat or in a solvent with $H_2NR^4$. The conversion of the 1-position H to $R^1$ in either alternative method may be conducted at room temperature under basic conditions with the $R^1$—halide and optionally with an alkali metal halide catalyst such as NaI. When $R^1$ is alkynyl and the triple bond is at the terminal position, and $R^1$ is to be inserted after formation of the pyrazolopyridine, Q in formula (IX) should be converted to $HNR^4$ prior to incorporation of the alkynyl $R^1$ since an explosion may occur if the alkynyl $R^1$ is in place during a high temperature, high pressure reaction with $H_2NR^4$.

In a further method, a compound of formula (VI) is reacted with N-bromosuccinimide to replace the $R^1$ group by H under conditions described above for the reaction of (VI) wherein X is alkoxy, also to replace $R^1$ by H. The thus-produced compound is of the formula (IX) wherein Q is chloro or bromo and may be converted to (VI) by reaction with $R^1$—Cl, $R^1$—I or $R^1$—Br as described above for the reaction of (IX) wherein Q is alkoxy with $R^1$—Cl, $R^1$—I or $R^1$—Br.

According to a further feature of the invention there is provided a process for the preparation of the compounds of the formula (I), wherein R, $R^1$, $R^3$, $R^4$, $R^5$ and $R^6$ are as stated above unless otherwise stated, and the N-oxides at the 7-position of the pyrazolo[3,4-b]pyridine ring system, and the pharmaceutically-acceptable acid-addition salts thereof, which comprises:

a. esterifying a carboxylic acid of the formula (VIII) with a compound of the formula LG—$R^5$ wherein LG is a leaving group, for example a halo atom, for example a chlorine or bromine atom, in the presence of an acid-binding agent, for example an alkali metal carbonate;

b. reacting an acid halide, for example an acid chloride, of an acid of the formula (VIII), or an acid-addition salt of said acid halide, with an alcohol of the formula $R^5$—OH;

c. in the case where $R^1$ is an oxoalkyl radical, hydrolyzing under acidic conditions, for example in the presence of a hydrohalic acid, the corresponding compound of the formula (I) wherein $R^1$ is an alkyl radical which is substituted by a ketal, hemiketal, acetal or hemiacetal group;

d. in the case where $R^1$ is a hydroxyalkyl radical, reducing the corresponding compound of the formula (I) wherein $R^1$ stands for an oxoalkyl radical, for example by means of a borohydride derivative having reducing properties, for example sodium borohydride;

e. reacting a halo compound of the formula (X):

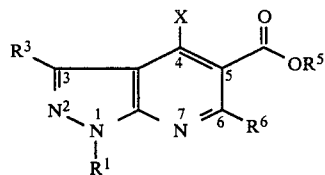

wherein X is halogen, with an amine of the formula $R^4NH_2$; or f. reacting a compound of the formula (IX):

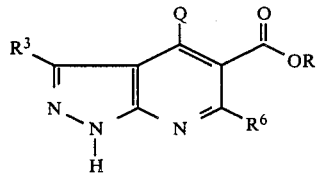

wherein Q is $HNR^4$ and R is a value of $R^5$, with a compound of the formula $R^1$—Cl, $R^1$—Br or $R^1$—I.

Further, it is apparent that compounds of the invention may be synthesized by conversion of a compound of formula (I) to another of formula (I), e.g., by oxidation of (I) wherein $R^1$ is hydroxy-substituted to yield one wherein $R^1$ is oxo-substituted alkyl, by methods known in the art.

Novel intermediates are also part of the present invention and include formulae (VI), (VII), (VIII) and (X) wherein $R^3$, $R^4$, X, R, $R^5$ and $R^6$ $L$ are as defined above and $R^1$ is cycloalkyl, cycloalkylalkyl, alkenyl, alkynyl, alkyl into which is inserted a divalent moiety selected from the group consisting of oxygen, sulfur, sulfinyl or sulfonyl, or alkyl substituted by a hydroxy, amino, alkylamino, dialkylamino, cyano, oxo, ketal, hemiketal, acetal or hemiacetal group or by one or more halogen atoms.

The compounds of the present invention of formula (I) are useful in the suppression of central nervous system activity in mammals, e.g., in humans, by suppression of convulsions, the relaxation of skeletal muscles, by inducing sleep, and particularly for the treatment of anxiety.

According to a further feature of the invention there are provided pharmaceutical compositions comprising at least one compound of the formula (I), wherein $R^1$, $R^3$, $R^4$, $R^5$ and $R^6$ are as defined above, or an N-oxide at the 7-position of the pyrazolo[3,4-b]pyridine ring system, or a pharmaceutically-acceptable acid-addition salt thereof, and a pharmaceutically-acceptable diluent or carrier.

The pharmaceutical compositions of the invention may be prepared and used according to methods known for the compounds cartazolate and tracazolate. Specifically, the new compounds of this invention are central nervous system depressants and may be used as tranquilizers or ataractic agents for the relief of anxiety and tension states, for example, in mice, cats, rats, dogs and other mamalian species such as man, in the same manner as chlordiazepoxide. For this purpose a compound or mixture of compounds of formula (I), or a pharmaceutically-acceptable acid-addition salt thereof, may be administered orally or parenterally in a conventional dosage form such as tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula (I) will be at least about 0.1 mg/kg of body weight per day for mammals with a maximum dosage for a small mammal such as a dog, of about 100 mg/kg per day. For humans, a dosage of about 0.1 to 50 mg/kg per day will be effective, e.g., about 5 to 2500 mg/day for an average man. The dosage can be given once daily or in divided doses, e.g., 2 to 4 doses daily, and such will depend on the duration and maximum level of activity of a particular compound. The dose may be conventionally formulated in an oral or parenteral dosage form by compounding about 10 to 250 mg per unit of dosage of conventional, vehicle, excipient, binder, preservative, stabilizer, flavor or the like as called for by accepted pharmaceutical practice, e.g., as described in U.S. Pat. No. 3,755,340.

Among the tests conducted to demonstrate the anxiolytic activity of the present compounds was the Shock-Induced Suppression of Drinking (Rats) (SSD) Test described in Pharmacology Biochemistry and Behavior, Vol. 12, pages 819-821 (1980) which was carried out as follows:

Male rats in the weight range of 200 to 220 grams are water-deprived for 48 hours and food-deprived for 24 hours before testing. Normally, the rats are orally intubated (5 ml/kg) with the test compound (based on mg/kg body weight). The vehicle control group of rats is also intubated by mouth. A positive control group of rats is also orally administered a control dose of 18 mg/kg of chlordiazepoxide. Randomization is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration was used, the protocol was identical except that the drugs were administered (5 ml/kg) 30 minutes prior to testing. The rat is placed on the floor in the chamber facing the licking tube. The animal is allowed 5 minutes to make 20 licking responses and receive the first shock (0.5 mA). If this does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

In the SSD test, the compound of the invention of formula (I) wherein $R^1$ is n-pentyl; $R^3$ is hydrogen; $R^4$ is hydrogen; $R^5$ is $-CH_2CH=CH_2$ or cyclopropylmethyl; and $R^6$ is methyl showed activity as indicated by a significant (less than 0.05, Students' t-test) increase in the number of shocks taken.

A second test for anxiolytic activity conducted on compounds of the invention was the [$^3$H]flunitrazepam binding test described in the European Journal of Pharmacology, Vol. 78, pages 315-322 (1982) by B. A. Meiners and A. I. Salama, which test is conducted as follows:

A lysed mitochrondrial-synaptosomal ($P_2$) fraction was prepared from the cerebral cortex of male Sprague-Dawley rats weighing 150-250 g according to the method of Braestrup and Squires in the Proceedings of the National Academy of Science U.S.A., Vol. 74, page 3805 (1977). The fraction was then washed twice by centrifugation in 50 mM Tris-HCl pH 7.4 buffer.

Specific flunitrazepam binding was measured by a filtration assay similar to that of Wastek et al. in the European Journal of Pharmacology, Vol. 50, page 445 (1978). The 2 ml assays contained 0.2 nM [$^3$H]flunitrazepam (84 Ci/mmol) and membranes equivalent to 10 mg fresh weight (0.2 mg protein) in 50 mM Tris-HCl pH 7.4 buffer. Test compounds were added in 10 μl 95% ethanol which was also added to the control. Nonspecific binding was determined in the presence of 2.5 μM clonazepam or 0.5 μM flunitrazepam. The samples were allowed to equilibrate for 90 min. at 0° C. before being filtered and rinsed. Typical assays were done in triplicate, and confained approximately 4000 cpm total and 150 cpm non-specific binding. Determinations of affinity and maximum binding were made by adding different amounts of non-radioactive flunitrazepam to 0.2 nM [$^3$H]flunitrazepam.

Anxiolytic activiity is indicated in the flunitrazepam binding test by a displacement of the flunitrazepam such as is exhibited by benzodiazepines and by enhancement of the binding such as is shown by cartazolate and tracazolate. In the flunitrazepam binding test, the compound of the invention wherein $R^1$ is n-pentyl; $R^3$ and $R^4$ are hydrogen; $R^5$ is $-CH_2CH=CH_2$ or cyclopropylmethyl; and $R^6$ is methyl showed activity as displacers of flunitrazepam binding.

None of the compounds of the formula (I) which have been tested in the above-mentioned tests has exhibited any sign of toxicity. Furthermore, the compound of the formula (I) described in Example 8 below has an approximate $LD_{50}$ in the rat of 800 mg/kg.

Synthesis of compounds of the invention is demonstrated by the following Examples, degrees being in Centigrade (C.) and the following abbreviations being used: mg (milligrams); kg (kilograms); g (grams); psi (pounds per square inch pressure); mM (millimoles); eq (equivalents); N (normal); rt (room temperature); ml (milliliters); DMF (dimethylformamide); THF (tetrayhdrofuran); EtOAc (ethyl acetate); $Et_2O$ (diethyl ether); MeOH (methanol); EtOH (ethanol); tlc (thin layer chromatography); mm (millimeters); bp (boiling point); NMR (nuclear magnetic resonance); MS (mass spectrum); m/e (mass to charge ratio); IR (infrared spectrum); and mp (melting point). Conventional chemical abbreviations for the elements, e.g., C, H, N, and O, are also used.

EXAMPLE 1 a. 5-Amino-1-n-pentylpyrazole (Formula (II), $R^1$=pentyl and $R^3$=H)

To a stirred solution of 40.27 g (0.473 mole) of cyanoethylhydrazine in 348 ml of toluene was added dropwise a solution of 42.8 g (0.497 mole) of valeraldehyde in 87 ml of toluene whereupon a slight exothermic reaction occurred. After stirring 3 hours at rt, the reaction mixture was concentrated to give 80.50 g of the intermediate hydrazone as an amber oil.

This oil was then added to a solution of sodium butoxide, prepared by dissolving 2.0 g (87 mg atoms) of sodium in 435 ml of n-butanol, heated at reflux for 5 hours. The resulting cooled solution was concentrated to leave 89.7 g of a dark viscous oil which was distilled to give 31.68 g of 5-amino-1-n-pentylpyrazole as a light yellow oil, bp=106°-112° at 0.35-0.4 mm of Hg; tlc, $R_f$=0.3, silica gel, EtOAc:hexane (1:1); MS, m/e=153.

b. 4-Hydroxy-6-methyl-1-pentyl-1H-pyrazolo[3,4-b]pyridine-5-carboxylic acid ethyl ester (Formula (IV), $R^1$=pentyl, $R^3$=H, R=$CH_2CH_3$, $R^6$=$CH_3$)

To 52 g of stirred polyphosphoric acid was added 12.02 g (78.4 mM) of the pyrazole produced in Example 1a and 15.86 g (78.4 mM) of diethyl acetylmalonate. The resulting mixture was then stirred at 120° for 3 hours, allowed to cool and then diluted with water with vigorous stirring. The resulting mixture was extracted with four portions of $Et_2O$ which were combined, dried with $MgSO_4$, filtered and concentrated to leave 18.25 g of the product ethyl ester as an amber oil which slowly crystallized. Recrystallization from hexane gave the product as a white solid; mp=49°-51° C.; tlc, $R_f$=0.4, silica gel, $Et_2O$:hexane (1:1); MS, m/e=291.

Elemental Analysis Calculated for $C_{15}H_{21}N_3O_3$: C, 61.84; H, 7.27; N, 14.42 Found: C, 61.64; H, 7.12; N, 14.56 c.
4-Chloro-6-methyl-1-pentyl-1H-pyrazolo[3,4-b]pyridine-5-carboxylic acid ethyl ester (Formula (VI), $R^1$=pentyl, $R^3$=H, X=Cl, R=$CH_2CH_3$, $R^6$=$CH_3$)

A solution of 1.05 g (3.60 mM) of the product of Example 1b and 4.5 ml (49 mM) of phosphorus oxychloride was refluxed for 3.2 hours and then concentrated to remove the excess phosphorus oxychloride. The residue was diluted with water and the resulting mixture extracted with $Et_2O$, dried with $MgSO_4$, filtered and concentrated to leave 0.83 g of the product as an amber oil; tlc, $R_f$=0.8, silica gel, $Et_2O$:hexane (1:1); MS, m/e=309, 311.

d.
4-Amino-6-methyl-1-pentyl-1H-pyrazolo[3,4-b]pyridine-5-carboxylic acid ethyl ester (Formula (VII), $R^1$=pentyl, $R^3$=H, $R^4$=H, R=$CH_2CH_3$, $R^6$=$CH_3$)

A solution of 14.02 g (45.3 mM) of the 4-chloro product from Example 1c in 80 ml of EtOH saturated with $NH_3$ was heated in a pressure vessel at 125°–130° C. for 10 hours. The cooled reaction mixture was concentrated and the residue was triturated with $Et_2O$ and filtered. The filtrate was dried with $MgSO_4$, filtered and concentrated to leave 12.85 g of the title product as a crystalline solid. The product was dissolved in $Et_2O$, passed through a short column of silica gel using $Et_2O$ as the eluent and concentrated to leave 12.20 g of the amino ester product as a white crystalline solid. Recrystallization from hexane gave 11.23 g of the product as white crystals; mp=55°–66° C.

Elemental Analysis Calculated for $C_{15}H_{22}N_4O_2$: C, 62.05; H, 7.64; N, 19.30 Found: C, 62.28; H, 7.68; N, 19.45 e.
4-Amino-6-methyl-1-pentyl-1H-pyrazolo[3,4-b]pyridine-5-carboxylic acid (Formula (VIII), $R^1$=pentyl, $R^3$=H, $R^4$=H, $R^6$=$CH_3$)

A solution of 13.50 g (46.5 mM) of the amino ester product of Example 1d and 7.36 g (184 mM) of NaOH in 329 ml of 95% EtOH was warmed at 45°–50° C. for 38 hours and then concentrated on a rotary evaporator to remove the EtOH. The residue was dissolved in 300 mls of water, filtered and acidified with acetic acid whereupon a white precipitate formed. The precipitate was collected, washed with water and air-dried to give 9.53 g of a white solid which was recrystallized from EtOAc to give 8.80 g of the title amino acid product as a white solid; mp=176°–176.5° C. (dec).

Elemental Analysis Calculated for $C_{13}H_8N_4O_2$: C, 59.52; H, 6.92; N, 21.36 Found: C, 59.29; H, 6.94; N, 21.30 f.
4-Amino-6-methyl-1-pentyl-1H-pyrazolo[3,4-b]pyridine-5-carboxylic acid allyl ester (Formula (I), $R^1$32 pentyl, $R^3$=H, $R^4$=H, $R^5$=$CH_2CH=CH_2$)

A mixture of 1.75 g (12.7 mM) of anhydrous $K_2CO_3$, 2.21 g (8.4 mM) of the amino acid product of Example 1e, 0.02 g of KI, and 1.02 g (8.43 mM) of allyl bromide in 21.6 ml of anhydrous DMF was stirred at room temperature for 1.5 hours and then poured into water. The resulting mixture was extracted with $Et_2O$ and the combined ether extracts were washed several times with water, dried with $MgSO_4$, filtered and concentrated to leave 2.56 g of an amber oil which crystallized. Recrystallization from hexane gave 2.27 g of the allyl ester title product as a white crystalline solid; mp=65.8°–67° C.

Elemental Analysis Calculated for $C_{16}H_{22}N_4O_2$: C, 63.55; H, 7.33; N, 18.53 Found: C, 63.28; H, 7.23; N, 18.39

EXAMPLE 2 a.
4-Amino-6-methyl-1-pentyl-1H-pyrazolo[3,4-b]pyridine-5-carboxylic acid chloride hydrochloride A stirred solution of 0.94 g (3.6 mM) of the amino acid product of Example 1e in 6.8 ml of thionyl chloride was warmed at 45°–50° C. for 1 hour and then concentrated to leave the acid chloride hydrochloride as a yellow solid.

b.
4-Amino-6-methyl-1-pentyl-1H-pyrazolo[3,4-b]pyridine-5-carboxylic acid 2-methoxyethyl ester hydrochloride The yellow solid title product of Example 2a was suspended in 10 ml of dry toluene and 16 ml of 2-methoxyethanol was added with stirring. After 12 hours, the reaction mixture was concentrated and the residue suspended in aqueous sodium bicarbonate and extracted with $Et_2O$. The combined ether extracts were washed with water, dried with $MgSO_4$, filtered and concentrated to give 1.01 g of a light amber oil. This oil was chromatographed over silica gel using $Et_2O$:hexane (6:1) to give 0.72 g of the desired title ester which was converted to its hydrochloride salt using ethereal HCl. The crude salt was recrystallized from EtOH/$Et_2O$ to give 0.65 g of the methoxyethyl ester title product as a white solid; mp=150°–152.5° C. (dec).

Elemental Analysis Calculated for $C_{16}H_{24}N_4O_3$.HCl: C, 53.85; H, 7.06; N, 15.70 Found: C, 53.72; H, 7.11; N, 15.91

EXAMPLE 3

4-Amino-6-methyl-1-pentyl-1H-pyrazolo[3,4-b]pyridine-5-carboxylic acid 2-propynyl ester The procedure of Example 1f was followed using 2.45 g (9.34 mM) of the amino acid product of Example 1e, 1.94 g (14.0 mM) of $K_2CO_3$, 24 ml of DMF, 1.11 g (9.34 mM) of parpargyl bromide (3-bromopropyne) and 0.02 g of KI. The procedure of Example 1f provided 2.70 g of the crude ester as a solid which was recrystallized from hexane to give 2.54 g of the propargyl ester title product as a white solid; mp=96°–96.8° C.

Elemental Analysis Calculated for $C_{16}H_{20}N_4O_2$: C, 63.98; H, 6.71; N, 18.65 Found: C, 63.88; H, 6.69; N, 18.81

EXAMPLE 4

4-Amino-6-methyl-1-pentyl-1H-pyrazolo[3,4-b]pyridine-5-carboxylic acid benzyl ester The procedure of Example 1f was followed using 0.99 g (3.8 mM) of the amino acid product of Example 1e, 0.79 g (5.7 mM) of $K_2CO_3$, 0.65 g (3.8 mM) of benzyl bromide and 9.7 ml of DMF to provide 1.23 g of the crude benzyl ester which was recrystallized from hexane to give 1.05 g of the benzyl ester title compound as a white solid; mp=66.5°–67° C.

Elemental Analysis Calculated for $C_{20}H_{24}N_4O_2$: C, 68.16; H, 6.86; N, 15.90 Found: C, 67.94; H, 6.93; N, 16.01

EXAMPLE 5

4-Amino-6-methyl-1-pentyl-1H-pyrazolo[3,4-b]pyridine-5-carboxylic acid 3-butenyl ester The procedure of Example 1f was followed using 1.01 g (3.85 mM) of the amino acid product of Example 1e, 0.80 g (5.8 mM) of $K_2CO_3$, 0.52 g (3.85 mM) of 1-bromo-3-n-butene butene and 9.9 ml of DMF with extension of the reaction time to 23 hours. The procedure resulted in 1.11 g of the crude ester as a yellow oil which slowly crystallized. Recrystallization from hexane gave 0.97 g of the butenyl ester title product as a white solid; mp=49.8°–51.0° C.

Elemental Analysis Calculated for $C_{17}H_{24}N_4O_2$: C, 64.53; H, 7.65; N, 17.71 Found: C, 64.79; H, 7.49; N, 17.64

EXAMPLE 6

4-Amino-6-methyl-1-pentyl-1H-pyrazolo[3,4-b]pyridine-5-carboxylic acid 2-chloro-2-propenyl ester The procedure of Example 1f was followed using 1.00 g (3.81 mM) of the amino acid product of Example 1e, 0.79 g (5.7 mM) of $K_2CO_3$, 0.42 g (3.8 mM) of 2,3-dichloro-1-propene, 0.04 g of KI and 9.8 ml of DMF with extension of the reaction time to 24 hours followed by 2.5 hours at 45°–50° C. The procedure of Example 1f provided 1.07 g of the crude ester as an off-white solid which was recrystallized from hexane to give 0.96 g of the title ester as white crystals; mp=79.2°–80.0° C.

Elemental Analysis Calculated for $C_{16}H_{21}ClN_4O_2$: C, 57.05; H, 6.28; N, 16.64 Found: C, 57.22; H, 6.35; N, 16.54

EXAMPLE 7

4-Amino-6-methyl-1-pentyl-1H-pyrazolo[3,4-b]pyridine-5-carboxylic acid 3-phenyl-2-propenyl ester The procedure of Example 1f was followed using 0.94 g (3.6 mM) of the amino acid product of Example 1e, 0.75 g (5.4 mM) of $K_2CO_3$, 0.71 g (3.6 mM) of cinnamyl bromide, 0.04 g of KI and 9.2 ml of DMF. The procedure of Example 1f gave 1.23 g of the crude ester as an off-white solid which was recrystallized from toluene to give 1.06 g of the cinnamyl ester title product as white crystals;
mp=123.8°–124.8° C.

Elemental Analysis Calculated for $C_{22}H_{26}N_4O_2$: C, 69.82; H, 6.92; N, 14.80 Found: C, 69.94; H, 6.97; N, 14.59

EXAMPLE 8

4-Amino-6-methyl-1-pentyl-1H-pyrazolo[3,4-b]pyridine-5-carboxylic acid cyclopropylmethyl ester The acid chloride hydrochloride product of Example 2a was prepared from 3.22 g (12.3 mM) of the corresponding amino acid as in Example 2a and was then suspended in 35 ml of toluene. To the stirred ice bath cooled suspension was added 8.9 g (123 mM) of cyclopropylcarbinol and the resulting reaction mixture was allowed to stir at rt overnight. The reaction mixture was then basified with triethylamine, filtered and the filtrate washed successively with water/acetic acid, water and aqueous sodium bicarbonate. After drying over $MgSO_4$, the organic material was filtered and concentrated to leave 3.82 g of the crude ester as a light yellow oil which crystallized. Recrystallization from hexane gave 3.19 g of the ester title product as a white solid; mp=62.5°–65.6° C.

Elemental Analysis Calculated for $C_{17}H_{24}N_4O_2$: C, 64.53; H, 7.65; N, 17.71 Found: C, 64.44; H, 7.78; N, 17.96

EXAMPLE 9

4-Amino-6-methyl-1-pentyl-1H-pyrazolo[3,4-b]pyridine-5-carboxylic acid cyclobutylmethyl ester The hydrochloride product of Example 2a was prepared from 1.10 g (4.19 mM) of the corresponding amino acid according to the procedure of Example 2a. The product was then suspended in 15 ml of toluene. To the stirred ice bath cooled suspension was added 3.08 g (35.8 mM) of cyclobutylcarbinol and the reaction mixture was then stirred at rt for 2 hours after which it was diluted with $Et_2O$ to form a precipitate. The precipitate was collected, suspended in aqueous sodium carbonate solution and shaken thoroughly with EtOAc until the solids dissolved. The organic layer was dried over $MgSO_4$ filtered and concentrated to leave 1.21 g of a clear oil which slowly crystallized. Recrystallization from hexane gave 1.12 g of the title product as white crystals; mp=73°–74° C.

Elemental Analysis Calculated for $C_{18}H_{26}N_4O_2$: C, 65.43; H, 7.93; N, 16.96 Found: C, 65.25; H, 7.77; N, 17.10.

EXAMPLE 10

4-Amino-6-methyl-1-pentyl-1H-pyrazolo[3,4-b]pyridine-5-carboxylic acid 2-butenyl ester The hydrochloride product of Example 2a was prepared from 1.27 g (4.84 mM) of the amino acid product of Example 1e according to the procedure of Example 2a and was then suspended in 14 ml of toluene. To the stirred ice bath cooled suspension was added 4.1 ml (48 mM) of crotyl alcohol (2-buten-1-ol) whereupon the solids slowly dissolved. The reaction mixture was then made basic with triethylamine and filtered to separate the precipitated triethylamine hydrochloride. The filtrate was diluted with $Et_2O$, washed with water, dried over $MgSO_4$, filtered and concentrated to provide 1.86 g of the crude ester as yellow oil which slowly crystallized. This product was chromatographed over silica gel with EtOAc:hexane (3:5) and the fractions containing the desired product were combined and concentrated to leave 1.26 g of the crotyl ester as a white solid. Recrystallization from hexane gave 0.99 g of the crotyl ester title product as white crystals; mp=78.7°–81.2° C.

Elemental Analysis Calculated for $C_{17}H_{24}N_4O_2$: C, 64.53; H, 7.65; N, 17.71 Found: C, 64.83; H, 7.83; N, 17.93

EXAMPLE 11 a. [[[(1-pentyl-5-pyrazolyl)amino]methylene]malonic acid diethyl ester (Formula (V), $R^1$=pentyl, $R^3$=H, R=$CH_2CH_3$)

A mixture of 15.56 g (101.5 mM) of 5-amino-1-n-pentylpyrazole and 21.96 g (101.5 mM) of diethyl ethoxymethylenemalenate was stirred and heated at 120° C. for 2 hours and then distilled to give 26.53 g of the enamine title product as a light yellow oil; bp=140°–150° C. at 0.04–0.05 mm of Hg; tlc, Rf=0.6, silica gel, EtOAc:hexane (1:1); MS, m/e=323.

b.
4-Hydroxy-1-pentyl-1H-pyrazolo[3,4-b]pyridine-5-carboxylic acid ethyl ester (Formula (IV), $R^1$=pentyl, $R^3$=H, $R$=$CH_2CH_3$, $R^6$=H)

A solution of 11.63 g (35.96 mM) of the product of Example 11a in 28.7 ml of diphenyl ether was heated at 235°–255° C. under a nitrogen atmosphere for 2 hours with provisions made to remove the EtOH formed by means of a Dean-Stark trap. The reaction mixture was concentrated to leave a dark solid residue which was recrystallized from toluene to give 2.53 g of the hydroxy ester title product as light tan crystals; mp=70°–71.5° C.

Elemental Analysis Calculated for $C_{14}H_{19}N_3O_3$: C, 60.63; H, 6.91; N, 15.15 Found: C, 60.63; H, 6.93; N, 15.33 c.
4-Chloro-1-pentyl-1H-pyrazolo[3,4-b]pyridine-5-carboxylic acid ethyl ester (Formula (VI), $R^1$=pentyl, $R^3$=H, $R$=$CH_2CH_3$, $R^6$=H)

A solution of 2.01 g (7.25 mM) of the product of Example 11b in 9.1 ml of phosphorus oxychloride was refluxed for 1 hour and then concentrated to remove the excess phosphorus oxychloride. The residue was diluted with water and the resulting mixture extracted with $Et_2O$. The combined organic extracts were washed with aqueous sodium bicarbonate, dried over $MgSO_4$, filtered and concentrated to leave 2.02 g of the chloro ester title product as a light amber oil; tlc, $R_f$=0.8, silica gel, $Et_2O$:hexane (1:1).

d.
4-Amino-1-pentyl-1H-pyrazolo[3,4-b]pyridine-5-carboxylic acid ethyl ester (Formula (VII), $R^1$=pentyl, $R^3$=H, $R^4$=H, $R$=$CH_2CH_3$, $R^6$=H):

The procedure of Example 1d was followed using 1.96 g (6.63 mM) of the product of Example 11c as the starting material with 11.5 ml of EtOH saturated with $NH_3$. The procedure of Example 1d gave 1.77 g of the crude amine ester which was recrystallized from toluene to give 1.46 g of the amine ester title product as white crystals; mp=148.5°–150.5° C.

Elemental Analysis Calculated for $C_{14}H_{20}N_4O_2$: C, 60.85; H, 7.30; N, 20.28 Found: C, 60.82; H, 7.06; N, 20.35 e. 4-Amino-1-pentyl-1H-pyrazolo[3,4-b]pyridine-5-carboxylic acid (Formula VIII), $R^1$=pentyl, $R^3$=H, $R^4$=H, $R^6$=H)

The procedure of Example 1e was followed using 8.14 g (29.5 mM) of the amino ester product of Example 11d, 4.67 g (117 mM) of NaOH and 209 ml of 95% aqueous EtOH. The procedure of Example 1e provided 6.79 g of the amino acid title product; mp=245°–246° C. (dec); tlc, $R_f$=0.3, silica gel, $CHCl_3$:MeOH (85:15); MS, m/e=248.

f.
4-Amino-1-pentyl-1H-pyrazolo[3,4-b]pyridine-5-carboxylic acid allyl ester (Formula (I), $R^1$=pentyl, $R^3$=H, $R^4$=H, $R^5$=$CH_2CH=CH_2$, $R^6$=H)

The procedure of Example 1f was followed using 0.98 g (3.9 mM) of the amino acid produced in Example 11e, 0.80 g (5.8 mM) of potassium carbonate, 0.48 g (4.0 mM) of allyl bromide and 9.9 ml of DMF. The procedure of Example 1f provided 1.02 g of the crude ester which was recrystallized from toluene/hexane to give 0.92 g of the title allyl ester as white crystals; mp=147.2°–148.3° C.

Elemental Analysis Calculated for $C_{15}H_{20}N_4O_2$: C, 62.48; H, 6.99; N, 19.43 Found: C, 62.52; H, 7.11; N, 19.45

EXAMPLE 12 a. 5-Amino-1-(3-methylbutyl)pyrazole (Formula (II), $R^1$=$CH_2$—$CH_2CH(CH_3)_2$, $R^3$=H)

The procedure of Example 1a was followed using 26.14 g (303.5 mM) of isovaleraldehyde in 53 ml of toluene and 24.56 g (288.6 mM) of cyanoethylhydrazine in 202 ml of toluene to give 46.7 g of the intermediate hydrazone as an amber oil. This hydrazone was then cyclized to the aminopyrazole using the procedure of Example 1a using 1.1 g (48 mg atoms) of sodium in 265 ml of 1-butanol and extending the reflux period to 18 hours. Distillation of the crude aminopyrazole gave 20.93 g of 5-amino-1-(3-methylbutyl)pyrazole as a light yellow oil; bp=98°–101° C. at 0.3–0.35 mm of Hg; tlc, $R_f$=0.5, silica gel, $Et_2O$; MS, m/e=153.

b.
[[(1-(3-Methylbutyl)-5-pyrazolyl)amino]methylene]malonic acid diethyl ester (Formula (V), $R^1$=$CH_2CH_2CH(CH_3)_2$, $R^3$=H, $R$=$CH_2CH_3$)

The title compound was prepared according to the procedure of Example 11a utilizing the pyrazole produced in Example 12a as the starting material. The title compound was recovered as a light yellow oil; bp=140°–150° C. at 0.03–0.05 mm Hg.

c.
4-Hydroxy-1-(3-methylbutyl)-1H-pyrazolo[3,4-b]pyridine-5-carboxylic acid ethyl ester The title compound was prepared according to the procedure of Example 11b using as starting material the product of Example 12b. The title compound was recovered as tan crystals; mp=65°–70° C.

d.
4-Chloro-1-(3-methylbutyl)-1H-pyrazolo[3,4-b]pyridine-5-carboxylic acid ethyl ester The title compound was prepared as an amber oil according to the procedure of Example 11c using as starting material the product of Example 12c.

e.
4-Amino-1-(3-methylbutyl)-1H-pyrazolo[3,4-b]pyridine-5-carboxylic acid ethyl ester The title compound was prepared according to the procedure of Example 11d using as starting material the title compound of Example 12d. The product was obtained as the hydrochloride salt; mp=170°–176.6° C. (dec).

Elemental Analysis Calculated for $C_{14}H_{20}N_4O_2$ HCl: C, 53.76; H, 6.77; N, 17.91 Found: C, 53.70; H, 6.78; N, 17.90 f.
4-Amino-1-(3-methylbutyl)-1H-pyrazolo[3,4-b]pyridine-5-carboxylic acid The title compound was prepared according to the procedure of Example 11e using as starting material the free base product of Example 12e. The title compound had an mp=263.5°–264° C. (dec).

g.
4-Amino-1-(3-methylbutyl)-1H-pyrazolo[3,4-b]pyridine-5-carboxylic acid allyl ester The title compound was prepared according to the procedures of Examples 1f and 11f; mp=124°–126° C.

Elemental Analysis: Calculated for $C_{15}H_{20}N_4O_2$: C, 62.48; H, 6.99; N, 19.43 Found: C, 61.98; H, 6.88; N, 19.45

EXAMPLE 13

4-Amino-6-methyl-1-pentyl-1H-pyrazolo[3,4-b]pyridine-5-carboxylic acid 2-methyl-2-propenyl ester The procedure of Example 1f was followed using 1.01 g (3.85 mM) of the product of Example 1e, 0.80 g (5.8 mM) of $K_2CO_3$, 0.35 g (3.85 mM) of 1-chloro-2-methyl-2-propene, 9.9 ml of DMF and 0.01 g of KI with a reaction time of 24 hours. The procedure provided 0.92 g of the crude ester as a white solid which was recrystallized from hexane to give 0.85 g of the title compound as white crystals; mp=80°–81° C.

Elemental Analysis Calculated for $C_{17}H_{24}N_4O_2$: C, 64.53; H, 7.65; N, 17.71 Found: C, 64.74; H, 7.58; N, 17.72

EXAMPLE 14

4-Amino-6-methyl-1-pentyl-1H-pyrazolo[3,4-b]pyridine-5-carboxylic acid 1-methyl-2-propenyl ester The procedure of Example 1f was followed using 1.14 g (4.34 mM) of the product of Example 1e, 0.90 g (6.5 mM) of $K_2CO_3$, 0.40 g (4.4 mM) of 3-chloro-1-butene, 0.06 g of KI and 11.2 ml of DMF at 60°–65° C. for 18 hours. The procedure provided 0.92 g of the crude ester as a yellow oil which could be crystallized from hexane to give 0.80 g of the title compound as an off-white solid; mp=64.6°–67.2° C.

Elemental Analysis Calculated for $C_{17}H_{24}N_4O_2$: C, 64.53; H, 7.65; N, 17.71 Found: C, 64.63; H, 7.86; N, 17.33

EXAMPLE 15

4-Amino-6-methyl-1-(3-methylbutyl)-1H-pyrazolo[3,4-b]-pyridine-5-carboxylic acid allyl ester The procedure of Examples 1a through 1e was followed using $(CH_3)_2CHCH_2CHO$ in the place of valeraldehyde to yield the amino acid of formula (VIII) wherein $R^1$ is $CH_2CH_2CH(CH_3)_2$, $R^3$ and $R^4$ are H and $R^6$ is $CH_3$. The procedure of Example 1f was then followed using the thus-produced amino acid product in an amount of 0.88 g (3.4 mM), 0.45 g (3.7 mM) of 1-bromo-2-propene, 0.70 g (5.1 mM) of $K_2CO_3$, 0.03 g of KI and 9.6 ml of DMF. The procedure provided 0.95 g of the crude ester as an off-white solid which was recrystallized from hexane to give 0.82 g of the title product as white crystals; mp=89.3°–90.2° C.

Elemental Analysis Calculated for $C_{16}H_{22}N_4O_2$: C, 63.55; H, 7.33; N, 18.53 Found: C, 63.44; H, 7.39; N, 18.47

EXAMPLE 16

4-Amino-6-methyl-1-(3-methylbutyl)-1H-pyrazolo[3,4-b]-pyridine carboxylic acid cyclopropylmethyl ester The procedure of Example 9 was followed using 1.20 g (4.58 mM) of the amino acid of formula (VIII) described in Example 15, 8.7 ml of thionyl chloride and 3.71 ml of cyclopropylcarbinol and $CH_2Cl_2$ in the place of toluene. The procedure provided the title product which was recrystallized from hexane to yield 0.85 g of a white solid; mp=70°–71° C.

Elemental Analysis Calculated for $C_{17}H_{24}N_4O_2$: C, 64.53; H, 7.65; N, 17.71 Found: C, 64.46; H, 7.58; N, 17.86

EXAMPLE 17 a. 5-Amino-1-(3-methylpentyl)pyrazole (Formula (II), $R^1=CH_2CH_2CH(CH_3)CH_2CH_3$, $R^3=H$)

The procedure of Example 1a was followed using $CH_3CH_2CH(CH_3)CH_2CHO$ in the place of valeraldehyde; bp=110° C. at 0.5 mm of Hg.

b.
4-Hydroxy-6-methyl-1-(3-methylpentyl)-1H-pyrazolo[3,4-b]-pyridine-5-carboxylic acid ethyl ester The title compound was prepared according to the procedure of Example 1b using the pyrazole product of Example 17a as the starting material.

c.
4-Chloro-6-methyl-1-(3-methylpentyl)-1H-pyrazlo[3,4-b]-pyridine-5-carboxylic acid ethyl ester The title compound was prepared according to the procedure of Example 1c using the title product of Example 17b as the starting material.

d.
4-Amino-6-methyl-1-(3-methylpentyl)-1H-pyrazolo[3,4-b]-pyridine-5-carboxylic acid ethyl ester The title compound was prepared according to the procedure of Example 1d using as starting material the product of Example 17c. The hydrochloride salt had mp=217°–222° C.

Elemental Analysis Calculated for $C_{16}H_{24}N_4O_2 \cdot HCl$: C, 56.38; H, 7.39; N, 16.44 Found: C, 56.32; H, 7.52; N, 16.57 e.
4-Amino-6-methyl-1-(3-methylpentyl)-1H-pyrazolo[3,4-b]-pyridine-5-carboxylic acid The title compound was prepared according to the procedure of Example 1e using as starting material the free base product of Example 17d.

f.
4-Amino-6-methyl-1-(3-methylpentyl)-1H-pyrazolo[3,4-b]-pyridine-5-carboxylic acid allyl ester The title compound was prepared according to the procedure of Example 1f using as starting material the product of Example 17e, tan crystals; mp=85°–86° C.

Elemental Analysis Calculated for $C_{17}H_{24}N_4O_2$: C, 64.53; H, 7.65; N, 17.71 Found: C, 64.55; H, 7.54; N, 17.91

EXAMPLE 18

4-Amino-6-methyl-1-pentyl-1H-pyrazolo[3,4-b]pyridine-5-carboxylic acid 1,1-dimethyl-2-propenyl ester The hydrochloride product of Example 2a was prepared from 0.96 g (3.7 mM) of the corresponding amino acid as in Example 2a and was then suspended in 10 ml of toluene. To the stirred suspension was added 3.2 g (37 mM) of 2-methyl-3-buten-2-ol and the reaction mixture was then processed as in Example 8 to provide 0.88 g of the crude ester as a tacky off-white solid. This material was chromatographed over silica gel with EtOAc:hexane (2:5). The fractions containing the desired product were combined and concentrated to leave 0.63 g of the ester as a clear oil which crystallized to a white solid. Recrystallizaton from hexane gave 0.50 g of the title product as white crystals; mp=77.7°–78.5° C.

Elemental Analysis Calculated for $C_{18}H_{26}N_4O_2$: C, 65.43; H, 7.93; N, 16.96 Found: C, 65.19; H, 8.00; N, 16.92

EXAMPLE 19 a.

4-Ethoxy-1-ethyl-6-methyl-1H-pyrazolo[3,4-b]pyridine-5-carboxylic acid ethyl ester 1-Ethyl-4-hydroxy-6-methyl-1H-pyrazolo[3,4-b]-pyridine-5-carboxylic acid ethyl ester was prepared according to Example 1b, using 5-amino-1-ethylpyrazole in place of 5-amino-1-n-pentylpyrazole, and 44 g (17.6 mM) of the hydroxy compound were dissolved in 250 ml of dry DMF. Ground anhydrous $K_2CO_3$ (26.1 g, 1.1 eq) was added to the DMF solution followed by the addition of ethyl iodide (14.5 ml, 1.1 eq). The reaction mixture was stirred at 60° C. for 4 hours at which time an additional 4.5 ml of ethyl iodide were added. The reaction mixture was stirred for an additional 3 hours and then cooled to rt. The mixture was poured into 1 liter of water and extracted three times with EtOAc, 300 ml each. The extracts were combined and washed twice with water, 500 ml each, and once with brine (500 ml). The organic layer was dried over anhydrous $MgSO_4$, filtered and evaporated to leave 47.21 g of a white solid; mp=55.5°–56.5° C.

b.

4-Ethoxy-6-methyl-1H-pyrazolo[3,4-b]pyridine-5-carboxylic acid ethyl ester

The compound prepared in Example 19a (10.5 g, 38 mM) was dissolved in 250 ml of $CCl_4$. N-Bromosuccinimide (14.8 g 2.2 eq) which had been recrystallized from water and dried over $P_2O_5$ under vacuum was added to the $CCl_4$ solution. The reaction mixture was heated to reflux while being irradiated with a sunlamp. After 3 hours of reflux the reaction was cooled to 0° C. The reaction mixture was filtered and the filtrate was concentrated to a yellow oil. The oil was dissolved in 80 ml THF to which was added 80 ml saturated sodium carbonate solution and 80 ml water. The mixture was stirred vigorously for 18 hours. The mixture was poured into 100 ml water and extracted with EtOAc. The extracts were dried over anhydrous sodium sulfate, filtered and evaporated down to a white solid which was recrystallized from EtOAc/hexane leaving the desired product as a white powder (6.75 g); mp=180°–182° C.; tlc, $R_f$=0.14, silica gel, EtOAc:hexane (1:1).

c.

4-Ethoxy-1-(3-hydroxypropyl)-6-methyl-1H-pyrazolo[3,4-b]pyridine-5-carboxylic acid ethyl ester The product of Example 19b (1.5 g, 6.0 mM) was dissolved in 25 ml dry DMF. Ground anhydrous $K_2CO_3$ (2.5 g, 3 eq) was added to the DMF solution and the mixture was stirred for 10 minutes. 3-Bromopropanol (1.66 g, 2 eq) from Aldrich Chemical Co. was then added all at once. The reaction was stirred for 3 hours at rt. The mixture was poured into 100 ml water and extracted with EtOAc. The organic layers were combined and washed with water and then with saturated NaCl solution. The extracts were dried over anhydrous $Na_2SO_4$, filtered and evaporated to leave an oil which crystallized under vacuum (1.52 g); tlc; $R_f$=0.21, silica gel, EtOAc:hexane (2:1).

d.

4-Ethoxy-1-(3-methoxypropyl)-6-methyl-1H-pyrazolo[3,4-b]pyridine-5-carboxylic acid ethyl ester A 50% suspension of sodium hydride in mineral oil (0.30 g, 1.25 eq) was washed three times with dry hexane. Freshly distilled THF (30 ml) was added to the sodium hydride. The alcohol prepared in Example 19c (1.52 g, 5.0 mM) was added in one portion to the reaction mixture. The mixture was stirred at rt until all evidence of hydrogen evolution had ceased. Methyl iodide (1.4 g, 5 eq) was added in one portion and the reaction was stirred vigorously for 18 hours. The mixture was poured into 100 ml of water and extracted with EtOAc. The organic extracts were combined, washed with saturated NaCl solution, dried over anhydrous sodium sulfate, filtered and evaporated, leaving an amber oil which was chromatographed over silica gel using EtOAc:hexane (1:1) as the eluent. The desired product was isolated as an oil (1.16 g); tlc, $R_f$=0.46, silica gel, EtOAc:hexane (2:1).

e.

4-Amino-1-(3-methoxypropyl)-6-methyl-1H-pyrazolo[3,4-b]pyridine-5-carboxylic acid ethyl ester The compound prepared in Example 19d (1.85 g, 5.76 mM) was placed in a 45 ml stainless steel pressure vessel and cooled to −78° C. Liquid $NH_3$ (15 ml) was added and the vessel was sealed and slowly warmed to rt. The reaction was then heated at 100° C. for 12 hours. The reaction vessel was then cooled to −78° C., vented, allowed to come to rt and opened. The oily residue was chromatographed over silica gel using EtOAc:hexane (1:1) as the eluent. The desired product was isolated as an oil (1.2 g); $R_f$=0.66, silica gel, EtOAc.

f.

4-Amino-1-(3-methoxypropyl)-6-methyl-1H-pyrazolo[3,4-b]pyridine-5-carboxylic acid allyl ester hydrochloride The compound prepared in Example 19e (1.1 g, 3.8 mM) was dissolved in 15 ml EtOH. A solution of NaOH (0.5 g in 10 ml water) was added to the EtOH solution. The mixture was stirred at 55° C. for 18 hours, cooled to rt and acidified with glacial acetic acid to pH=5 and poured into 25 ml water. The product was extracted with EtOAc. The organic layers were combined, dried over anhydrous sodium sulfate, filtered and evaporated to leave the crude carboxylic acid as a colorless oil. The oil was subsequently dissolved in 25 ml dry DMF. Ground anhydrous potassium carbonate (1.57 g, 3 eq) was added to the DMF solution, followed by the addition of allyl bromide (0.46 g, 1 eq). The mixture was stirred at rt for 2 hours. The reaction mixture was poured into 100 ml water and extracted with EtOAc. The organic layers were combined and washed twice with water and once with brine. The extracts were dried over anhydrous $Na_2SO_4$, filtered and evaporated leaving a clear oil. The oil was dissolved in 10 ml absolute EtOH and 10 ml $Et_2O$. Ethereal HCl was added dropwise until a white precipitate formed. The product was filtered off as a white solid (0.58 g); mp=197°–199° C.; MS, m/e=304.

Elemental Analysis Calculated for $C_{15}H_{20}N_4O_3.HCl$: C, 52.86; H, 6.21; N, 16.44 Found: C, 52.35; H, 6.29; N, 16.56

EXAMPLE 20 a.
4-Ethoxy-1-(2-ethoxyethyl)-6-methyl-1H-pyrazolo[3,4-b]pyridine-5-carboxylic acid ethyl ester The procedure of Example 19c was repeated using the compound prepared in Example 19b (1.2 g, 4.8 mM), anhydrous $K_2CO_3$ (1.99 g, 3 eq), and 2-bromoethyl ethyl ether (1.08 g, 2 eq) as the alkyl halide in 30 ml dry DMF. The reaction mixture was poured into water and extracted with EtOAc. The extracts were combined and dried over anhydrous sodium sulfate, filtered and evaporated leaving a mustard yellow oil (1.49 g); tlc, $R_f=0.56$, silica gel, EtOAc.

b.
4-Amino-1-(2-ethoxyethyl)-6-methyl-1H-pyrazolo[3,4-b]pyridine-5-carboxylic acid ethyl ester The compound prepared in Example 20a (1.49 g, 4.6 mM) was placed in a stainless steel pressure vessel with 15 ml of $NH_3$-saturated EtOH. The vessel was sealed and heated to 120° C. for 72 hours. The vessel was cooled to 0° C., vented and opened. The EtOH was evaporated off leaving a residue which was chromatographed on a silica gel column using EtOAc:hexane (1:2) as the eluent leaving the desired product as an oil; tlc, $R_f=0.46$, silica gel, EtOAc:hexane (2:1).

c.
4-Amino-1-(2-ethoxyethyl)-6-methyl-1H-pyrazolo[3,4-b]pyridine-5-carboxylic acid allyl ester The procedure of Example 19f was followed using 1 g of the product from Example 20b in 5 ml EtOH and 0.41 g of NaOH in 5 ml $H_2O$. The reaction mixture was stirred at 40° C. for 18 hours. The crude acid (0.52 g) was thereafter obtained as a white solid. The acid was dissolved in 8 ml dry DMF followed by the addition of ground anhydrous $K_2CO_3$ (0.51 g, 1.5 eq) and allyl bromide (0.30 g, 1.1 eq). The reaction mixture was stirred at rt for 1.5 hours and then poured into 50 ml water. The aqueous mixture was extracted with EtOAc. The extracts were combined and washed once with water and once with brine. The extracts were dried over anhydrous $Na_2SO_4$, filtered and evaporated to leave an oil which was crystallized from toluene/hexane leaving the desired product as beige crystals; mp=38°-40° C.; MS, m/e=304.

Elemental Analysis Calculated for $C_{15}H_{20}N_4O_3$: C, 59.20; H, 6.62; N, 18.41 Found: C, 58.79; H, 6.67; N, 18.28

EXAMPLE 21 a.
4-Ethoxy-1-(2-methoxyethyl)-6-methyl-1H-pyrazolo[3,4-b]pyridine-5-carboxylic acid ethyl ester The procedure of Example 19c was followed using the product of Example 19b (3 g, 12 mM), $K_2CO_3$ (5.50 g, 3.3 eq) and 40 ml DMF, and 2-methoxyethyl bromide (3.34 g, 2 eq) as the alkyl halide. The reaction mixture was stirred at rt for 60 hours. The work up resulted in an amber oil which was chromatographed over silica gel using EtOAc:hexane (1:1) as the eluent leaving the product as a colorless oil (2.68 g); tlc, $R_f=0.45$, silica gel, EtOAc.

b.
4-Amino-1-(2-methoxyethyl)-6-methyl-1H-pyrazolo[3,4-b]pyridine-5-carboxylic acid ethyl ester The procedure of Example 19e was followed using the material prepared in Example 21a (2.5 g, 8.0 mM) as the starting material. The product was scraped from the pressure vessel as a white solid (2.17 g); mp=82°-85° C.; tlc, $R_f=0.39$, silica gel, EtOAc.

c.
4-Amino-1-(2-methoxyethyl)-6-methyl-1H-pyrazolo[3,4-b]pyridine-5-carboxylic acid allyl ester hydrochloride The procedure of Example 19f was followed using the material prepared in Example 21b (2.0 g, 7 mM) dissolved in 15 ml EtOH and NaOH (0.86 g, 3 eq) in 10 ml water. The reaction was allowed to proceed at rt for 18 hours. The carboxylic acid was isolated as colorless oil (1.6 g). The oil was dissolved in 25 ml dry DMF, and ground $K_2CO_3$ (1.1 g, 1.5 eq) was added followed by allyl bromide (0.64 g, 1 eq). The reaction mixture was stirred at rt for 1 hour. The hydrochloride salt was isolated as a white solid (0.24 g); mp=194.5°-196° C.; MS, m/e=290.

Elemetal Analysis Calculated for $C_{14}H_{18}N_4O_3.HCl$: C, 51.45; H, 5.86; N, 17.15 Found: C, 51.43; H, 5.94; N, 16.94

EXAMPLE 22 a.
4-Amino-6-methyl-1H-pyrazolo[3,4-b]pyridine-5-carboxylic acid ethyl ester The procedure of Example 19e was followed using the compound prepared in Example 19b (6.0 g, 24 mM) as the substrate. The resulting solid was scraped out of the reaction vessel and recrystallized from DMF leaving the desired product (4.35 g) as a white solid which decomposes over 295° C.

b.
4-Amino-6-methyl-1-propargyl-1H-pyrazolo[3,4-b]pyridine-5-carboxylic acid ethyl ester The procedure of Example 19c was followed using the product of Example 22a and 2 eq of propargyl bromide. The reaction time was extended to 72 hours. The reaction products were chromatographed over silica gel using EtOAc:hexane (1:1) as the eluent. The title compound was obtained as a yellow solid; tlc, $R_f=0.36$, silica gel, $CHCl_3$:MeOH (93.7).

c. 4-Amino-1-(allenyl and propargyl)-6-methyl-1H-pyrazolo[3,4-b]pyridine-5-carboxylic acid allyl ester The procedure of Example 20c was followed using the product from Example 22b and allowing the reaction to proceed at rt. The title compounds were obtained as a yellow solid which was recrystallized from toluene/hexane; mp=150°-153° C., MS, m/e=270; NMR data showed a ratio of products of 2:1 (allenyl:propargyl), characteristic $^1H$ NMR peaks for the 1-propargyl product were, in delta units, 2.36 (triplet, 1H), and 5.2 (doublet, 2H) and for the allenyl product, 5.68 (doublet, 2H) and 7.7 (triplet, 1H).

Elemental Analysis Calculated for $C_{14}H_{14}N_4O_2$: C, 62.20; H, 5.22; N, 20.73 Found: C, 62.47; H, 5.47; N, 20.04

EXAMPLE 23 a.
4-Amino-1-(5-hexynyl)-6-methyl-1H-pyrazolo[3,4-b]pyridine-5-carboxylic acid ethyl ester The procedure of Example 19c was followed using the product of Example 22a and 1-iodo-5-hexyne. The reaction products were chromatographed over silica gel using EtOAc:hexane (1:1) as the eluent. The title compound was obtained as a white solid; mp=63°–65° C.; tlc, $R_f$=0.49, silical gel, EtOAc:hexane (1:1).

b.
4-Amino-1-(5-hexynyl)-6-methyl-1H-pyrazolo[3,4-b]pyridine-5-carboxylic acid allyl ester The procedure of Example 20c was followed using the product of Example 23a and acidifying the reaction mixture to pH=1 with 3N HCl in place of glacial acetic acid. The carboxylic acid precipitated as a white solid, was filtered off and air dried. The title compound was obtained as a white solid; mp=69°–70° C.; MS, m/e=312; tlc, $R_f$=0.45, silica gel, EtOAc:hexane (1:1).

Elemental Analysis Calculated for $C_{17}H_{20}N_4O_2$: C, 65.36; H, 6.45; N, 17.94 Found: C, 65.07; H, 6.36; N, 17.95

EXAMPLE 24 a.
4-Amino-1-(3-butynyl)-6-methyl-1-H-pyrazolo[3,4-b]pyridine-5-carboxylic acid ethyl ester The procedure of Example 19c was followed using the product of Example 22a (3.17 g, 14 mM) and 1-iodo-3-butyne (5 g, 1.2 eq). The reaction products were chromatographed over silica gel using EtOAc:hexane (1:1) as the eluent. The product was crystallized from toluene/hexane leaving the title compound as an amber solid; mp=101°–103° C.; tlc, $R_f$=0.73, silica gel, EtOAc.

b.
4-Amino-1-(3-butynyl)-6-methyl-1H-pyrazolo[3,4-b]pyridine-5-carboxylic acid allyl ester The procedure of Example 20c was followed using the product of Example 24a. The title compound was obtained as white platelets; mp=115°–116° C.; MS, m/e=284.

Elemental Analysis Calculated for $C_{15}H_{16}N_4O_2$: C, 63.36; H, 5.67; N, 19.70 Found: C, 63.32; H, 5.67; N, 19.36

EXAMPLE 25 a.
4-Ethoxy-1-[2-(ethylthio)ethyl]-6-methyl-1H-pyrazolo[3,4-b]pyridine-5-carboxylic acid ethyl ester The procedure of Example 19c was followed using the product of Example 19b and 2-chloroethyl ethyl sulfide and the addition of 1.7 molar percent of NaI. The reaction products were chromatographed over silica gel using EtOAc:hexane (1:1) as the eluent. The title compound was obtained as an amber oil; tlc, $R_f$=0.66, silica gel, EtOAc:hexane (1:1).

b.
4-Amino-1-[(2-ethylthio)ethyl]-6-methyl-1H-pyrazolo[3,4-b]pyridine-5-carboxylic acid ethyl ester The procedure of Example 19e was followed using the product of Example 25a. The title compound was obtained as an oil; tlc, $R_f$=0.52, silica gel, EtOAc:hexane (1:1).

c.
4-Amino-1-[2-(ethylthio)ethyl]-6-methyl-1H-pyrazolo[3,4-b]pyridine-5-carboxylic acid allyl ester hydrochloride The procedure of Example 19f was followed using the product of Example 25b. The title compound was obtained as its HCl salt by dissolving the final product in 1:1 EtOH:Et$_2$O and adding ethereal HCl. The title compound was obtained as a white solid; mp=197°–199° C., MS, m/e=304.

Elemental Analysis Calculated for $C_{15}H_{20}N_4O_3 \cdot HCl$: C, 52.86; H, 6.21; N, 16.44 Found: C, 52.34; H, 6.28; N, 16.56

EXAMPLE 26 a.
1-[2-(ethylthio)ethyl]-4-ethoxy-6-methyl-1H-pyrazolo[3,4-b]pyridine-5-carboxylic acid ethyl ester, S-oxide The product of Example 25a (2.5 g, 7.4 mM) was dissolved in 65 ml CH$_2$Cl$_2$ at 0° C. m-Chloroperoxybenzoic acid (1.7 g, 1.12 eq) was added in portions over several minutes. The reaction mixture was stirred at 25° C. for 15 minutes. The reaction was quenched with 2 ml of saturated sodium sulfite solution. The CH$_2$Cl$_2$ was evaporated and replaced with EtOAc. The EtOAc solution was washed twice with 10% Na$_2$CO$_3$ solution and once with saturated NaCl solution. The organic extract was dried over Na$_2$SO$_4$, filtered and evaporated leaving the title compound as a clear oil which crystallized upon standing; mp=64°–66° C.; tlc, $R_f$=0.43, silica gel, EtOAc.

b.
4-Amino-1-[2-(ethylthio)ethyl]-6-methyl-1H-pyrazolo[3,4-b]pyridine-5-carboxylic acid ethyl ester, S-oxide The procedure of Example 19e was followed using the product of Example 26a and adjusting the reaction time to 13 hours. The product was obtained as a white solid; $R_f$=0.11, silica gel, CHCl$_3$:MeOH (93:7).

c.
4-Amino-1-[2-(ethylthio)ethyl]-6-methyl-1H-pyrazolo[3,4-b]pyridine-5-carboxylic acid allyl ester, S-oxide hydrochloride The procedure of Example 19f was followed using the product of Example 26b and acidifying the solution with 10% HCl solution and evaporating the EtOH and water resulting in a residue which was dried under vacuum. The residue was taken up in dry DMF. K$_2$CO$_3$ and allyl bromide were added and the mixture was stirred at 50° C. overnight. The reaction was quenched with water and extracted with EtOAc. The extracts were dried over Na$_2$SO$_4$, filtered and evaporated leaving a clear oil. The oil was chromatographed over silica gel using EtOAc:MeOH (9:1) as the eluent. The resulting oil was dissolved in 15 ml EtOH and 10 ml Et$_2$O was added. The solution was treated with ethereal HCl. The EtOH and Et$_2$O were evaporated leaving a white solid which was recrystallized from EtOH/hexane leaving the title compound as a white powder; mp=162°–163° C.; MS, m/e=336.

Elemental Analysis Calculated for $C_{15}H_{20}N_5SO_3 \cdot HCl$: C, 48.31; H, 5.68; N, 15.03 Found: C, 48.52; H, 5.87; N, 14.66

EXAMPLE 27 a.
4-Ethoxy-1-[2-(ethylthio)ethyl]-6-methyl-1H-pyrazolo[3,4-b]pyridine-5-carboxylic acid ethyl ester, S,S-dioxide The product of Example 25a (2.5 g, 7.5 mM) was dissolved in 5 ml glacial acetic acid. Hydrogen peroxide (30%, 3.6 molar) was added dropwise. The reaction mixture was refluxed for 1 hour. The reaction mixture was neutralized with saturated $Na_2CO_3$ solution and extracted with EtOAc. The extracts were washed once with 10% sodium sulfite solution, once with brine, dried over anhydrous $Na_2SO_4$, filtered and evaporated, leaving the sulfone as a white solid, mp=86°-88° C.; tlc, $R_f$=0.11, silica gel, EtOAc:hexane (1:1).

b.
4-Amino-1-[2-(ethylthio)ethyl]-6-methyl-1H-pyrazolo[3,4-b]pyridine-5-carboxylic acid ethyl ester, S,S-dioxide The procedure of Example 19e was followed using the product of Example 27a. The title compound was obtained crude as a sticky tan solid; $R_f$=0.5, silica gel, EtOAc.

c.
4-Amino-1-[2-(ethylthio)ethyl]-6-methyl-1H-pyrazolo[3,4-b]pyridine-5-carboxylic acid allyl ester, S,S-dioxide The procedure of Example 20c was followed using the product of Example 27b and 3N HCl to acidify the EtOH, hydroxide solution. The acid was isolated as a white powder, mp=204°-206° C. The ester was prepared following the procedure of Example 19f. The title compound was obtained as beige crystals; mp=107°-108° C.; MS, m/e=352.

Elemental Analysis Calculated for $C_{15}H_{20}N_4O_4S$: C, 51.12; H, 5.72; N, 15.90 Found: C, 51.27; H, 5.58; N, 15.88

EXAMPLE 28 a.
4-Ethoxy-1-(3-ethoxypropyl)-6-methyl-1H-pyrazolo[3,4-b]pyridine-5-carboxylic acid ethyl ester The procedure of Example 19d was followed using the alcohol prepared in Example 19c and ethyl iodide. The reaction mixture was chromatographed over silica gel using EtOAc:hexane (1:1) as the eluent. The title compound was obtained as a clear oil; tlc, $R_f$=0.40, silica gel, EtOAc:hexane (1:1).

b.
4-Amino-1-(3-ethoxypropyl)-6-methyl-1H-pyrazolo[3,4-b]pyridine-5-carboxylic acid ethyl ester The procedure of Example 19e was followed using the product of Example 28a. The title compound was obtained crude, tlc, $R_f$=0.17, silica gel, EtOAc:hexane (1:1).

c.
4-Amino-1-(3-ethoxypropyl)-6-methyl-1-H-pyrazolo[3,4-b]pyridine-5-carboxylic acid allyl ester hydrochloride The procedure of Example 19f was followed using the product of Example 28b holding the reaction temperature at 55° C. in both steps. The title compound was isolated as a white solid; mp=172°-174° C.

Elemental Analysis Calculated for $C_{16}H_{22}N_4O_3 \cdot HCl$: C, 54.15; H, 6.53; N, 15.79 Found: C, 53.94; H, 6.78; N, 15.81

EXAMPLE 29 a.
4-Ethoxy-6-methyl-1-(3-n-pentynyl)-1H-pyrazolo[3,4-b]pyridine-5-carboxylic acid ethyl ester The procedure of Example 19c was followed using the product of Example 19b and 1-bromo-3-pentyne as the alkylating agent and a catalytic amount of NaI. The reaction was stirred at 40° C. for 72 hours. The product mixture was chromatographed over silica gel using EtOAc:hexane (1:1) as the eluent. The title compound was obtained as a white solid; mp=94°-95° C.

b.
4-Amino-6-methyl-1-(3-n-pentynyl)-1H-pyrazolo[3,4-b]pyridine-5-carboxylic acid ethyl ester The procedure of Example 19e was followed using the product from Example 29a. The reaction time was adjusted to 13 hours. The title compound was obtained as a white solid; tlc, $R_f$=0.64, silica gel, EtOAc.

c.
4-Amino-6-methyl-1-(3-n-pentynyl)-1H-pyrazolo[3,4-b]pyridine-5-carboxylic acid allyl ester The procedure of Example 20c was followed using the product of Example 29b and allowing the first step to proceed at rt. The acid precipitated as a white solid upon acidification with 3N HCl. The second step was allowed to proceed at 40° C. The title compound was obtained as a tan solid; mp=113.5°-115° C.; MS, m/e=298.

Elemental Analysis Calculated for $C_{16}H_{18}N_4O_2$: C, 64.41; H, 6.08; N, 18.78 Found: C, 65.05; H, 6.17; N, 19.26

EXAMPLE 30 a.
4-Ethoxy-6-methyl-1-(cis-2-pentenyl)-1H-pyrazolo[3,4-b]pyridine-5-carboxylic acid ethyl ester The procedure of Example 19c was followed using the product of Example 19b and 1-bromo-cis-2-pentene. The mixture was chromatographed over silica gel using EtOAc:hexane (1:1) as the eluent. The title compound was obtained as an amber solid; tlc, $R_f$=0.55, EtOAc:hexane (1:1).

b.
4-Amino-6-methyl-1-(cis-2-pentenyl)-1H-pyrazolo[3,4-b]pyridine-5-carboxylic acid ethyl ester The procedure of Example 19e was followed using the product of Example 30a. The title compound was obtained crude as an amber oil; tlc, $R_f$=0.39, silica gel, EtOAc:hexane (1:1).

c.
4-Amino-6-methyl-1-(cis-2-pentenyl)-1H-pyrazolo[3,4-b]pyridine-5-carboxylic acid allyl ester The procedure of Example 20c was followed using the product of Example 30b and acidifying with 3N HCl instead of acetic acid. The carboxylic acid was obtained as a white solid. In the esterification, the temperature was 50° C. The title compound was obtained as a tan solid; mp=78°–81° C.; tlc, $R_f$=0.33, silica gel, EtOAc:hexane (1:2); MS, m/e=300.

Elemental Analysis Calculated for $C_{16}H_{20}N_4O_2$: C, 63.98; H, 6.71; N, 18.66 Found: C, 63.72; H, 6.64; N, 18.60

EXAMPLE 31 a.
4-Ethoxy-1-(4-methoxybutyl)-6-methyl-1H-pyrazolo[3,4-b]pyridine-5-carboxylic acid ethyl ester The procedure of Example 19c was followed using the product of Example 19b and 1-bromo-4-methoxybutane with a reaction time of 72 hours. The product mixture was chromatographed over silica gel using EtOAc:hexane (1:2) as the eluent. The title compound was obtained as a clear oil; tlc, $R_f$=0.63, silica gel, EtOAc.

b.
4-Amino-1-(4-methoxybutyl)-6-methyl-1H-pyrazolo[3,4-b]pyridine-5-carboxylic acid ethyl ester The procedure of Example 19e was followed using the product of Example 31a. The title compound was obtained as a white solid; tlc, $R_f$=0.48, silica gel, EtOAc:hexane (1:1).

c.
4-Amino-1-(4-methoxybutyl)-6-methyl-1H-pyrazolo[3,4-b]pyridine-5-carboxylic acid allyl ester hydrochloride The procedure of Example 19f was followed using the product of Example 31b for 72 hours stirring at rt. Upon acidification with 3N HCl the carboxylic acid precipitated as a white solid. The title compound was obtained as a white solid; mp=173°–174° C.; MS, m/e=318.

Elemental Analysis Calculated for $C_{16}H_{22}N_4O_3 \cdot HCl$: C, 54.15; H, 6.53; N, 15.79 Found: C, 53.91; H, 6.42; N, 15.79

EXAMPLE 32 a.
1-Benzyl-4-ethoxy-6-methyl-1H-pyrazolo[3,4-b]pyridine-5-carboxylic acid ethyl ester The procedure of Example 19c was followed using 1.5 g (6.0 mM) of the product of Example 19b, 2.5 g (18 mM) of $K_2CO_3$, 1.24 g (7.23 mM) of benzyl bromide, and 10 ml of DMF. An oil was obtained which was chromatographed over silica gel using EtOAc:hexane (1:3) as the eluent. The desired product was isolated as an oil (1.40 g); tlc, $R_f$=0.84, silica gel, EtOAc:hexane (1:1), which crystallized on standing.

b.
4-Amino-1-benzyl-6-methyl-1H-pyrazolo[3,4-b]pyridine-5-carboxylic acid ethyl ester A solution of 1.38 g (4.07 mM) of the product of Example 32a in 15 ml of EtOH saturated with $HN_3$ was heated in a pressure vessel at 120° for 17 hours. The cooled reaction mixture was concentrated and the residue chromatographed over silica gel using EtOAc:hexane (1:1) as the eluent. The desired product was isolated as a white solid (0.82 g); tlc, $R_f$=0.74, silica gel, EtOAc:hexane (1:1).

c.
4-Amino-1-benzyl-6-methyl-1H-pyrazolo[3,4-b]pyridine-5-carboxylic acid allyl ester The procedure of Example 19f was followed using 0.82 g (2.64 mM) of the product of Example 32b, 5 ml of EtOH, 0.21 g (5.25 mM) of NaOH and 4.1 ml of water. The crude carboxylic acid was a white solid which was reacted with 0.38 g (2.75 mM) of $K_2CO_3$, 0.32 g (2.66 mM) of allyl bromide, and 10 ml of DMF. The crude product, a yellow oil which crystallized on standing, was dissolved in EtOAc, filtered to remove insolubles, and evaporated to dryness. The residue was recrystallized from toluene/hexane to afford the desired product as white needles; mp=107.5°–108° C.; tlc, $R_f$=0.78, silica gel, EtOAc:hexane (1:1).

Elemental Analysis Calculated for $C_{18}H_{18}N_4O_2$: C, 67.07; H, 5.63; N, 17.38 Found: C, 66.83; H, 5.77; N, 17.56

EXAMPLE 33 a.
1-(4-Cyanobutyl)-4-ethoxy-6-methyl-1H-pyrazolo[3,4-b]pyridine-5-carboxylic acid ethyl ester The procedure of Example 19c was followed using 1.1 g (4.4 mM) of the product of Example 19b, 2.5 g (18 mM) of $K_2CO_3$, 0.86 g (5.3 mM) of 5-bromovaleronitrile, and 8 ml of DMF. The product was a white solid which was chromatographed over silica gel using EtOAc as the eluent. The desired product was isolated as a white solid (1.15 g); tlc, $R_f$=0.30, silica gel, EtOAc:hexane (1:1).

b.
4-Amino-1-(4-cyanobutyl)-6-methyl-1H-pyrazolo[3,4-b]pyridine-5-carboxylic acid ethyl ester The procedure of Example 19c was followed using 1.15 g (3.48 mM) of the product of Example 33a, the reaction being carried out at 100°–120° C. for 12 hours to afford a viscous syrup which was homogeneous to tlc, $R_f$=0.21, silica gel, EtOAc:hexane (1:1). The crude product was not purified by chromatography but was transferred from the pressure vessel in EtOH solution. The solution was concentrated to afford a slowly-crystallizing, viscous syrup (1.25 g); tlc, $R_f$=0.21, silica gel, EtOAc:hexane (1:1).

c.
4-Amino-1-(4-cyanobutyl)-6-methyl-1H-pyrazolo[3,4-b]pyridine-5-carboxylic acid allyl ester The procedure of Example 19f was followed using 1.64 g (5.44 mM) of the crude product of Example 33b, 10 ml of EtOH, 0.37 g (9.25 mM) of NaOH, and 3.7 ml of water. The crude carboxylic acid, 1.28 g of white solid, was reacted with 1.0 g (7.2 mM) of $K_2CO_3$, 0.70 g (5.8 mM) of allyl bromide, and 10 ml of DMF to afford 1.20 g of viscous oil. This oil was chromatographed over silica gel with EtOAc:hexane (1:1) affording a white solid which was recrystallized from toluene/hexanes to give 0.92 g of the title compound as white crystals; mp=87.5°–88.5° C.

Elemental Analysis Calculated for $C_{16}H_{19}N_5O_2$: C, 61.33; H, 6.11; N, 22.35 Found: C, 61.00; H, 6.13; N, 22.71

EXAMPLE 34 a.

4-Ethoxy-1-[4-(1,2-ethylenedioxy)pentyl]-6-methyl-1H-pyrazolo[3,4-b]pyridine-5-carboxylic acid ethyl ester The procedure of Example 19c was followed using 6.60 g (26.5 mM) of the product of Example 19b, 19.3 g (140 mM) of $K_2CO_3$, 5.80 g (35.2 mM) of 5-chloro-2-pentanone ethylene ketal, and 31 ml of DMF, with the following exceptions: 2.4 g (16 mM) of NaI was added to promote the reaction, and the reaction was carried out at 40°–45° C. for two days. The procedure afforded a brown oil which was chromatographed over silica gel using EtOAc:hexane (1:1) as the eluent. The desired product was isolated as a white solid (6.25 g); mp=84°–87° C.; $R_f$=0.27, silica gel, EtOAc:hexane (1:1).

b.

4-Amino-1-(4-(1,2-ethylenedioxy)pentyl)-6-methyl-1H-pyrazolo[3,4-b]pyridine-5-carboxylic acid ethyl ester The procedure of Example 19e was followed using 5.61 g (14.9 mM) of the product of Example 34a, with the reaction being carried out for 15 hours. The crude product, a slowly-crystallizing syrup (5.20 g), did not require chromatographic purification; tlc, $R_f$=0.19, silica gel, EtOAc:hexane (1:1).

c.

4-Amino-1-[4-(1,2-ethylenedioxy)pentyl]-6-methyl-1H-pyrazolo[3,4-b]pyridine-5-carboxylic acid allyl ester The procedure of Example 19f was followed, using 5.20 g (14.9 mM) of the crude product of Example 34b, 2.4 g (60 mM) of NaOH, 33 ml of EtOH and 24 ml of water, with the reaction being carried out at 40°–45° C. for three days. The product was isolated after evaporation of the EtOH from the reaction mixture, acidifying the aqueous residue with 10% HCl and saturating the resulting solution with NaCl to facilitate extraction of the product. There were thus isolated 4.74 g of the crude acid as a white solid, which was further reacted using 6.0 g (43 mM) of $K_2CO_3$, 2.31 g (19.1 mM) of allyl bromide, and 30 ml of DMF. The crude product, 5.48 g of slowly-crystallizing yellow oil, was identical by tlc, $R_f$=0.32, silica gel, EtOAc:hexane (1:1), to an analytical sample prepared previously be recrystallization from toluene/hexane, which showed mp=49.5° C. and which analyzed as follows:

Elemental Analysis Calculated for $C_{18}H_{24}N_4O_4$: C, 59.99; H, 6.71; N, 15.55 Found: C, 59.98; H, 6.66; N, 15.45

EXAMPLE 35

4-Amino-6-methyl-1-(4-oxo-n-pentyl)-1H-pyrazolo[3,4-b]-pyridine-5-carboxylic acid allyl ester To a solution of the ketal product of Example 34c (5.48 g, 15.2 mM) in 32 ml of MeOH was added 7 ml of 10% HCl, and the solution was stirred at rt under $N_2$ for 15 hours. The resulting white suspension was cooled to 0° C., and saturated aqueous $Na_2CO_3$ was added until the pH exceeded 9. The product was extracted with EtOAc, and the combined EtOAc layers were dried over anhydrous $Na_2SO_4$. Evaporation of the solvents afforded a yellow oil which was dissolved in EtOAc and filtered to remove insolubles. The solvent was evaporated, and the residue recrystallized from toluene/hexane to afford 4.08 g of light tan, large crystals. A second recrystallization of 3.0 g of this product from methyl tert-butyl ether/hexane gave 2.78 g of white crystals; mp=75°–78° C.

Elemental Analysis Calculated for $C_{16}H_{20}N_4O_3$: C, 60.75; H, 6.37; N, 17.71 Found: C, 60.50; H, 6.32; N, 17.78

The hydrochloride was prepared by treating an EtOH solution of the title compound with ethereal HCl. Recrystallization of the precipitate from EtOH containing a minor amount of $DMF/Et_2O$ afforded white crystals; mp=189°–192° C.

Elemental Analysis Calculated for $C_{16}H_{21}N_4O_3Cl$: C, 54.47; H, 6.00; N, 15.88 Found: C, 54.45; H, 5.98; N, 15.93

EXAMPLE 36

4-Amino-1-(4-hydroxypentyl)-6-methyl-1H-pyrazolo[3,4-b]pyridine-5-carboxylic acid allyl ester To a solution of the ketone product of Example 35 (0.94 g, 2.97 mM) in 9 ml of absolute EtOH, cooled to 0° C., was added 0.23 g (6.08 mM) of $NaBH_4$. The solution was stirred at 0° for 20 minutes, whereupon the excess of borohydride was destroyed by the cautious dropwise addition of saturated aqueous ammonium chloride. The mixture was allowed to warm to rt with stirring. After 15 minutes, saturated aqueous $Na_2CO_3$ was added until pH 9 was indicated by test papers, the mixture was poured into 10 ml of water, and the mixture extracted with EtOAc until no further product was evident in the organic phase. The combined extracts were dried over anhydrous sodium sulfate and evaporated to afford a clear oil which was dissolved in a minimum volume of EtOH at 0° C. Ethereal HCl was then added, and the resulting precipitate was collected and recrystallized from $EtOH/Et_2O$ to afford 0.75 g of white crystals; mp=169°–170° C. (decomposed).

Elemental Analysis Calculated for $C_{16}H_{22}N_4O_3 \cdot HCl$: C, 54.15; H, 6.53; N, 15.79 Found: C, 53.71; H, 6.52; N, 15.52

EXAMPLE 37 a.

4-Amino-6-methyl-1-(4-pentynyl)-1H-pyrazolo[3,4-b]pyridine-5-carboxylic acid ethyl ester The procedure of Example 19c was followed, using 1.2 g (5.5 mM) of the product of Example 22a, 1.5 g (10.9 mM) of potassium carbonate, 1.25 g (6.45 mM) of 1-iodo-4-pentyne and 10 ml of DMF, with the exception that the reaction was carried out at 40°–45° C. for 22 hours. The oil product was chromatographed over silica gel using EtOAc:hexane as the eluent. The title compound was isolated as a white solid (0.66 g); tlc, $R_f$=0.27, silica gel, EtOAc:hexane (1:1).

b.

4-Amino-6-methyl-1-(4-pentynyl)-1H-pyrazolo[3,4-b]pyridine-5-carboxylic acid allyl ester The procedure of Example 19f was followed, using 0.81 g (2.8 mM) of the product of Example 37a, 0.23 g (5.7 mM) of NaOH, 6 ml of EtOH, and 2.3 ml of water. There was isolated 0.73 g of the crude acid as a white solid, which was reacted with 0.78 g (5.7 mM) of potassium carbonate, 0.42 g (3.5 mM) of allyl bromide, and 6 ml of DMF to afford 0.81 g of the product as a white solid, which was chromatographed over a short column of silica gel with EtOAc. The product was then recrystallized from toluene/hexane to give 0.75 g of white flakes; mp=99.5° C.

Elemental Analysis Calculated for $C_{16}H_{18}N_4O_2$: C, 64.41; H, 6.08; N, 18.78 Found: C, 64.42; H, 6.19; N, 18.97

EXAMPLE 38 a.

1-Allyl-4-ethoxy-6-methyl-1H-pyrazolo[3,4-b]pyridine-5-carboxylic acid ethyl ester The procedure of Example 19c was followed using 2.20 g (8.83 mM) of the product of Example 19b, 2.92 g (21.2 mM) of potassium carbonate, and 10 ml of DMF to yield an oil which was chromatographed over silica gel with EtOAc:hexane (1:1). The title compound was obtained as a slightly orange oil (1.26 g); tlc, $R_f$=0.78, silica gel, EtOAc:hexane (1:1).

b.

1-Allyl-4-amino-6-methyl-1H-pyrazolo[3,4-b]pyridine-5-carboxylic acid ethyl ester The procedure of Example 19e was followed using 1.2 g (4.1 mM) of the product of Example 38a, with the exception that the white semisolid crude product (1.1 g) did not require chromatographic purification; tlc, $R_f$=0.63, silica gel, EtOAc:hexane (1:1).

c.

1-Allyl-4-amino-6-methyl-1H-pyrazolo[3,4-b]pyridine-5-carboxylic acid allyl ester The procedure of Example 19f was followed, using 1.05 g (4.03 mM) of the product of Example 38b, 0.33 g (8.3 mM) of NaOH, 10 ml of EtOH and 3.3 ml of water, the reaction mixture being acidified with 10% HCl instead of acetic acid. There was thus obtained 0.85 g of the crude carboxylic acid as a slightly yellowish solid, which was reacted with 1.01 g (7.3 mM) of potassium carbonate, 0.55 g (4.5 mM) of allyl bromide, and 8 ml of DMF. The crude product was chromatographed over silica gel, using EtOAc:hexane (1:1) as the eluent. The title compound was then obtained by recrystallization from toluene/hexanes (0.66 g) as white needles; mp=115.5° C.

Elemental Analysis Calculated for $C_{14}H_{16}N_4O_2$: C, 61.75; H, 5.92; N, 20.57 Found: C, 61.59; H, 5.92; N, 20.35

EXAMPLE 39 a.

1-(3-Butenyl)-4-ethoxy-6-methyl-1H-pyrazolo[3,4-b]pyridine-5-carboxylic acid ethyl ester The procedure of Example 19c was followed using 2.23 g (8.95 mM) of the product of Example 19b, 2.63 g (19.1 mM) of potassium carbonate, 1.38 g (10.2 mM) of 4-bromo-1-butene and 10 ml of DMF, the reaction being allowed to proceed for 8 hours, whereupon an additional 0.6 g (4.4 mM) of 4-bromo-1-butene was added and the reaction was allowed to proceed for an additional 13 hours. The title compound was obtained (1.71 g) as a viscous oil; tlc, $R_f$=0.80, silica gel, EtOAc:hexane (1:1).

b.

4-Amino-1-(3-butenyl)-6-methyl-1H-pyrazolo[3,4-b]pyridine-5-carboxylic acid ethyl ester The procedure of Example 19e was followed, using 1.71 g (5.64 mM) of the product of Example 39a, with the exception that the yellowish semisolid product (1.5 g) did not require chromatographic purification; tlc, $R_f$=0.68, silica gel, EtOAc:hexane (1:1).

c.

4-Amino-1-(3-butenyl)-6-methyl-1H-pyrazolo[3,4-b]pyridine-5-carboxylic acid allyl ester The procedure of Example 19f was followed using the product of Example 39b to afford a crude product which was chromatographed over silica gel using EtOAc:hexane (1:1) as the eluent. Recrystallization from toluene/hexane afforded the title compound; mp=64.0°-64.5° C.

Elemental Analysis Calculated for $C_{15}H_{18}N_4O_2$: C, 62.92; H, 6.34; N, 19.57 Found: C, 62.74; H, 6.32; N, 19.33

EXAMPLE 40 a.

4-Ethoxy-6-methyl-1-(4-pentenyl)-1H-pyrazolo[3,4-b]pyridine-5-carboxylic acid ethyl ester The procedure of Example 19c was followed using the product of Example 19b and 5-bromo-1-pentene, with the exception that the reaction was carried out at 50°-60° C. for 24 hours using two molar equivalents of the bromopentene. The crude product was chromatographed over silica gel using EtOAc:hexane (1:4) as the eluent to afford the title compound as a clear oil; tlc, $R_f$=0.45, silica gel, EtOAc:hexane (1:2).

b.

4-Amino-6-methyl-1-(4-pentenyl)-1H-pyrazolo[3,4-b]pyridine-5-carboxylic acid ethyl ester The procedure of Example 19e was followed using the product of Example 40a to provide the title compound as a clear oil; tlc, $R_f$=0.63, silica gel, EtOAc:hexane (1:1), which slowly crystallized on standing.

c.

4-Amino-6-methyl-1-(4-pentenyl)-1H-pyrazolo[3,4-b]pyridine-5-carboxylic acid allyl ester The procedure of Example 19f was followed using the product of Example 40b. Recrystallization of the product from toluene/hexanes provided the title compound as white crystals; mp=62.0°-62.5° C.

Elemental Analysis Calculated for $C_{16}H_{20}N_4O_2$: C, 63.98; H, 6.71; N, 18.65 Found: C, 64.12; H, 6.74; N, 18.65

EXAMPLE 41 a.

1-(3-Cyanopropyl)-4-ethoxy-6-methyl-1H-pyrazolo[3,4-b]pyridine-5-carboxylic acid ethyl ester A solution of 4-chlorobutyronitrile (2.5 g, 24 mM) and KI (4.0 g, 24 mM) in 15 ml of DMF was warmed to 70° C. with stirring under nitrogen for one hour. Finely ground anhydrous potassium carbonate (4.0 g, 29 mM) and the product of Example 19b (3.0 g, 12 mM) were added, and the mixture was stirred at 60°-70° C. for 7 hours, then for 16 hours at 40°-45° C. The mixture was poured into 100 ml of water and extracted with EtOAc until no further product was evident in the organic extracts. The combined extracts were dried over anhydrous $MgSO_4$ and evaporated to afford a crude product which was chromatographed over silica gel using EtOAc:hexane (1:1) as the eluent. The title compound (1.44 g) was obtained as a white solid; mp=99° C.; tlc, $R_f$=0.32, silica gel, EtOAc:hexane (1:1).

b.
4-Amino-1-(3-cyanopropyl)-6-methyl-1H-pyrazolo[3,4-b]pyridine-5-carboxylic acid ethyl ester The procedure of Example 19e was followed using the product of Example 41a to afford the title compound as a yellow syrup which slowly crystallized on standing; tlc, $R_f$=0.17, silica gel, EtOAc:hexane (1:1).

c.
4-Amino-1-(3-cyanopropyl)-6-methyl-1H-pyrazolo[3,4-b]pyridine-5-carboxylic acid allyl ester The procedure of Example 19f was followed using the product of Example 41b with the exception that four molar equivalents of NaOH were used at a temperature of 40°–45° C. to afford a mixture of carboxylic acid intermediates, owing to partial hydrolysis of the nitrile moiety. This mixture was not separated but was further reacted to provide a mixture of allyl ester products. The title compound was obtained by chromatography of the mixture over silica gel, eluting with EtOAc:hexane (1:1), following by recrystallization from toluene/hexane to provide white crystals; mp=86.0° C.

Elemental Analysis Calculated for $C_{15}H_{17}N_5O_2$: C, 60.19; H, 5.72; N, 23.40 Found: C, 60.61; H, 5.61; N, 23.20

EXAMPLE 42 a.
4-Ethoxy-6-methyl-1-(3-methyl-2-butenyl)-1H-pyrazolo[3,4-b]pyridine-5-carboxylic acid ethyl ester The compound prepared in Example 19b (2.0 g, 6.3 mM) was dissolved in 35 ml dry DMF. Ground anhydrous potassium carbonate (2.6 g, 3 eq) was added to the DMF solution followed by the addition of 1-bromo-3-methyl-but-2-ene (1.5 ml, 2 eq). The reaction mixture was stirred at rt for 4 hours, poured into 400 ml water and extracted twice with $Et_2O$, 100 ml each. The extracts were combined and washed twice with water, 200 ml each. The organic layer was dried over anhydrous $MgSO_4$, filtered and evaporated, leaving a dark amber liquid which was chromatographed over silica gel using $Et_2O$:hexane (1:1) as the eluent. The desired product was isolated as a yellow solid (1.18 g); tlc, $R_f$=0.37, silica gel, $Et_2O$:hexane (1:1).

b.
4-Amino-6-methyl-1-(3-methyl-2-butenyl)-1H-pyrazolo[3,4-b]pyridine-5-carboxylic acid ethyl ester The compound prepared in Example 42a (3.0 g, 9.6 mM) was reacted according to Example 19e. The resulting solid was recrystallized from toluene leaving the desired product (1.97 g) as an off-white solid; tlc, $R_f$=0.44, silica gel, $Et_2O$:hexane (7:3).

Elemental Analysis Calculated for $C_{15}H_{20}N_4O_2$: C, 62.48; H, 6.99; N, 19.43 Found: C, 62.64; H, 6.94; N, 19.40 c.
4-Amino-6-methyl-1-(3-methyl-2-butenyl)-1H-pyrazolo[3,4-b]pyridine-5-carboxylic acid The compound prepared in Example 42b (1.95 g, 6.8 mM) was dissolved in 22 ml EtOH. A solution of 1.1 g NaOH in 2 ml $H_2O$ was then added. The reaction mixture was stirred at 64° C. for 16 hours. The reaction mixture was cooled to rt, EtOH was evaporated, and the mixture was acidified to pH 6 with 1N HCl solution. The product was extracted into $CH_2Cl_2$ and washed with 50% brine solution. The organic layer was dried over anhydrous $MgSO_4$, filtered and evaporated, giving 1.29 g of an off-white solid; tlc, $R_f$=0.33, silica gel, $CH_2Cl_2$:MeOH (5:1); mp=174°–176° C.

d.
1-Amino-6-methyl-1-(3-methyl-2-butenyl)-1H-pyrazolo[3,4-b]pyridine-5-carboxylic acid allyl ester The compound prepared in Example 42c (1.29 g, 5.0 mM) was dissolved in 13 ml dry DMF. A catalytic amount of KI and finely ground potassium carbonate (1.03 g, 1.5 eq) were added, followed by addition of allyl bromide (0.60 g, 1 eq). The reaction mixture was vigorously stirred at rt for 5 hours. The mixture was filtered, poured into $H_2O$ and extracted into $Et_2O$. The organic layer was washed several times with $H_2O$, dried over anhydrous $MgSO_4$, filtered and evaporated, giving a solid that was chromatographed over silica gel using $Et_2O$:hexanes (3:2) as the eluent. The desired product was recrystallized from hexane, then isolated as a white solid (1.01 g); tlc, $R_f$=0.29, silica gel, $Et_2O$:hexane (3:2); IR (Nujol) 1710(s)cm$^{-1}$; mp=76°–78° C.; $^1$H NMR ($CDCL_3$, TMS, in delta units):2.8 (singlet, 3H), 5.0 (doublet, 2H) and 7.9 (singlet, 1H).

Elemental Analysis Calculated for $C_{16}H_{20}N_4O_2$: C, 63.98; H, 6.71; N, 18.65 Found: C, 63.83; H, 6.86; N, 18.78

EXAMPLE 43 a. 1-Bromo-3-methyl-3-butene

The title compound was prepared by mixing 7.75 ml (75.0 mM) 3-methyl-3-buten-1-ol and 2.06 ml (25.5 mM) pyridine at −40° C. Slowly, to maintain the reaction temperature below −30° C., were added 2.40 ml (25.5 mM) phosphorus tribromide dropwise. Mechanical stirring was necessary as the reaction mixture became very thick. After warming to rt, the reaction mixture was stirred 3 hours, diluted with 20 ml $Et_2O$, washed three times with $H_2O$, 10 ml each, and dried over $MgSO_4$. After filtration, the volatiles were distilled. Product was distilled to yield 2.95 g (26.4%) of a colorless liquid, bp=45° C. at 40 mm of Hg.

b.
4-Chloro-6-methyl-1H-pyrazolo[3,4-b]pyridine-5-carboxylic acid ethyl ester

A mixture of 10.0 g (37.4 mM) of 4-chloro-1-ethyl-6-methyl-1H-pyrazolo[3,4-b]pyridine-5-carboxylic acid ethyl ester, prepared according to Examples 1b and 1c from 5-amino-1-ethylpyrazole in place of 5-amino-1-pentylpyrazole, and 7.65 g (43.0 mM) of N-bromosuccinimide in 75 ml of carbon tetrachloride was illuminated with a sunlamp and stirred under $N_2$ at gentle reflux for 2 hours. The cooled reaction mixture was filtered and the filtrate concentrate to leave an orange residue which was dissolved in 50 ml of THF. 35 ml of saturated aqueous sodium carbonate were added, and the mixture was stirred vigorously at rt for 18 hours and then diluted with water and extracted with EtOAc. The combined extracts were dried with MgSO$_4$, filtered and concentrated to leave a white solid which was chromatographed over silica gel using the solvent system of EtOAc:hexane (1:3) as the eluant. The fractions containing the desired product were combined and concentrated to leave a white solid. Recrystallization of the solid from toluene/hexane gave 4.88 g of the desired ester as white needles, mp=156°-157.5° C.; tlc, R$_f$=0.2, silica gel, EtOAc:hexane (1:3).

c.
4-Chloro-6-methyl-1-(3-methyl-3-butenyl)-1H-pyrazolo[3,4-b]pyridine-5-carboxylic acid ethyl ester The title compound was prepared by adding 6.83 g (49.4 mM) powdered anhydrous K$_2$CO$_3$ and 3.95 g (16.5 mM) of the product of Example 43b to 40 ml DMF under N$_2$, followed by the addition of 2.70 g (18.1 mM) of the product of Example 43a. After vigorously stirring for 2.5 hours, the reaction mixture was poured into 25 ml water, extracted into Et$_2$O, dried over MgSO$_4$, filtered and concentrated to a brown oil. The oil was chromatographed over silica gel using the solvent system EtOAc:hexane (1:3) as the eluent to yield 3.57 g (70%) of a clear oil; tlc, R$_f$=0.7, silica gel, EtOAc:hexane (1:3).

d.
4-Amino-6-methyl-1-(3-methyl-3-butenyl)-1H-pyrazolo[3,4-b]pyridine-5-carboxylic acid ethyl ester A solution of 3.57 g (11.6 mM) of the product of Example 43c in 20 ml EtOH saturated with NH$_3$ was heated in a pressure vessel at 100° C. for 10 hours. The cooled reaction mixture was concentrated and the residue was triturated with Et$_2$O and filtered. The filtrate was dried with MgSO$_4$, filtered and concentrated to leave 3.34 g of the title compound as an off-white solid; tlc, R$_f$=0.2, silica gel, EtOAc:hexane (1:3).

e.
4-Amino-6-methyl-1-(3-methyl-3-butenyl)-1H-pyrazolo[3,4-b]pyridine-5-carboxylic acid A solution of 3.34 g (11.6 mM) of the product of Example 43d and 2.32 g (58.0 mM) of NaOH in 15 ml MeOH and 10 ml water was warmed at 40° C. for 24 hours and then concentrated on a rotary evaporator. The residue was taken up in 25 ml water, washed with Et$_2$O, and acidified with acetic acid whereupon an off-white precipitate formed. The precipitate was collected, washed with water and air-dried to yield 1.32 g (44%) of an off-white solid.

f.
4-Amino-6-methyl-1-(3-methyl-3-butenyl)-1H-pyrazolo[3,4-b]pyridine-5-carboxylic acid allyl ester To a stirring suspension of 1.04 g (7.49 mM) powdered K$_2$CO$_3$, 1.30 g (4.99 mM) of the product of Example 43e, a catalytic amount of KI and 10 ml DMF was added dropwise 0.43 ml (4.99 mM) allyl bromide. The reaction mixture was stirred at rt for 1 hour, taken up in water, extracted into Et$_2$O, washed several times with water, dried over MgSO$_4$, filtered and concentrated to a brown oil. The oil was chromatographed over silica gel using EtOAc:hexane (1:3) as the eluent. Recrystallization from hexane gave 0.90 g (60%) of the title compound as a white solid; mp=68°-69° C.; tlc, R$_f$=0.2, EtOAc:hexane (1:3).

Elemental Analysis Calculated for C$_{16}$H$_{20}$N$_4$O$_2$: C, 63.98; H, 6.71; N, 18.65 Found: C, 63.80; H, 6.81; N, 18.70

EXAMPLE 44 a. 1-(2-Hydroxyethyl)cyclopropyl phenyl sulfide

To 75 ml THF was added 5.50 g (36.6 mM) cyclopropyl phenyl sulfide which was prepared according to B. M. Trost, Journal of the American Chemical Society, Vol. 99, page 3080 (1977). The solution was cooled to 0° C. and 34.1 ml (43.9 mM) of n-butyl lithium were added dropwise. After stirring 2 hours, the reaction mixture was cooled to −78° C. and 5% Li$_2$CuCl$_4$, freshly made by stirring 0.16 g (3.66 mM) lithium chloride and 0.25 g (1.83 mM) copper (II) chloride in 2 ml THF for 5 minutes at rt, was added. After stirring 5 minutes, 2.20 ml (43.9 mM) condensed ethylene oxide was distilled into the reaction mixture, which was stirred 30 minutes at −78° C., 1 hour at 0° C., and 1 hour at rt. Quenching with 50 ml H$_2$O was followed by extracting into Et$_2$O, drying and concentrating to a brownish oil. The oil was chromatographed over silica gel with EtOAc:hexane (3:17) as the eluent. Kugelrohr distillation yielded 5.28 g (74%) of a colorless oil; tlc, R$_f$=0.2, silica gel, EtOAc:hexane (3:17); bp=85° C. at 0.2 mm of Hg.

b. 2-Cyclopropylethyl alcohol

To 90 ml condensed NH$_3$ in an EtOH bath was added 3.44 g (17.7 mM) of the product of Example 44a. Na (1.83 g, 79.7 mM) was added in small chunks allowing decolorization before the next chunk addition. After stirring 1 hour with the blue color from the last addition of sodium remaining, a catalytic amount of ferric nitrate was added. The reaction mixture turned gray. Cautiously, 5.21 g (97.4 mM) solid NH$_4$Cl was added along with 50 ml Et$_2$O. Following evaporation of NH$_3$, H$_2$O was carefully added and the reaction mixture was made basic with NaOH pellets, extracted into Et$_2$O, washed once with 10% NaOH, washed once with saturated NaCl, dried over Na$_2$SO$_4$ and distilled to yield 1.23 g (80%) of a clear oil; bp=55° C. at 35 mm of Hg.

c. 2-Bromoethylcyclopropane

To a rt suspension of 19.1 g (72.6 mM) triphenylphosphine and 12.6 g (90.8 mM) K$_2$CO$_3$ in 120 ml CH$_2$Cl$_2$ was added via dropping funnel 3.72 ml (72.6 mM) Br$_2$. The reaction was exothermic and precipitated PPh$_3$Br$_2$. The PPh$_3$Br$_2$ suspension was cooled to 0° C. and 5.22 g (60.5 mM) of the alcohol prepared in Example 44b were added. After stirring 2 hours, 0.65 ml (19.3 mM) MeOH were added to discharge excess PPh$_3$Br$_2$. Pentane (100 ml) was added to precipitate triphenylphosphine oxide. The reaction mixture was then heated under reflux for 30 minutes, filtered and volatiles distilled to yield a colorless liquid.

d.
4-Chloro-6-methyl-1-(2-cyclopropylethyl)-1H-pyrazolo[3,4-b]pyridine-5-carboxylic acid ethyl ester The title compound was prepared according to the procedure of Example 43c using the pyrazolopyridine product of Example 43b and the bromoethylcyclopropane of Example 44c, giving a 90% yield of the product as a clear oil; tlc, R$_f$=0.6, silica gel, EtOAc:hexane (1:3).

e. 4-Amino-6-methyl-1-(2-cyclopropylethyl)-1H-pyrazolo[3,4-b]pyridine-5-carboxylic acid ethyl ester The title compound was prepared according to the procedure of Example 43d using the product of Example 44d with the exception that the reaction time was extended to 15 hours. The amino ester was obtained in a 66% yield as a clear oil; tlc, $R_f=0.25$, silica gel, EtOAc:hexane (1:3).

f. 4-Amino-6-methyl-1-(2-cyclopropylethyl)-1H-pyrazolo[3,4-b]pyridine-5-carboxylic acid The title compound was prepared according to the procedure of Example 43e using the amino ester from Example 44e, with the exception that 10% HCl was used to acidify to pH 3 instead of glacial acetic acid. The title acid was obtained as an off-white solid in an 84% yield.

g. 4-Amino-6-methyl-1-(2-cyclopropylethyl)-1H-pyrazolo[3,4-b]pyridine-5-carboxylic acid allyl ester The title compound was prepared according to Example 43f using the product of Example 44f. The title ester was obtained as a white solid; mp=81°-83° C.; tlc, $R_f=0.2$, silica gel, EtOAc:hexane (1:3).

Elemental Analysis Calculated for $C_{16}H_{20}N_4O_2$: C, 63.98; H, 6.71; N, 18.65 Found: C, 63.81; H, 6.68; N, 18.42

EXAMPLE 45 a. Ethyl 3-hydroxy-4,4,4-trifluorobutyrate

A solution of 19.31 g of ethyl trifluoroacetoacetate (Fairfield Chemical) in 50 ml of ethyl acetate was hydrogenated at 3 atmospheres on a Parr shaker over (0.5 g) $PtO_2$ as a catalyst. The volatiles were removed and the residue distilled under high vacuum to afford 14.75 g (76%) of the title compound as a low melting solid. bp=47°-49° C. at 0.1 mm of Hg, mp (uncorrected)=about 25° C.

b. Ethyl 4,4,4-trifluorobutenoate

To a stirring solution of 22.0 g (118 mM) of the hydroxyester prepared in Example 45a. and 18.4 ml (130 mM) triethylamine in 100 ml ether at 0° C. was added 10.1 ml (130 mM) of methanesulfonyl chloride. The reaction was stirred one hour at 0° C., then diluted with an equal volume of pentane and filtered through celite. The solvents were removed at room temperature: no heat was applied. The remaining oil was dissolved in ether and cooled to 0° C. With mechanical stirring, 21.2 ml (142 mM) of 1,8 -diazabicyclo[5.4.0]undec-7-ene were added. The reaction was warmed to room temperature and stirred 3 hours. The yellow residue was dissolved by addition of 1% aqueous HCl and the solution extracted with ether. The organic phase was washed with 10% HCl, $CuSO_4$, and saturated sodium chloride, then dried over magnesium sulfate and filtered. The volatiles were removed. The title ester was distilled to yield 15.8 g (79.7%) of colorless liquid, bp=115°-120° C.

c. 4,4,4-Trifluorobutyric acid

A solution of 20.6 g (123 mM) unsaturated ester prepared in Example 45b. in 10 ml absolute ethanol was added to a stirring solution of 2.53 g (66.9 mM) sodium borohydride in 250 ml of absolute ethanol at 0° C. The mixture was kept at room temperature for 1.5 hours. Sodium hydroxide, 12.3 g (308 mM), in 20 ml $H_2O$ was added and the mixture heated at 40° C. for 1 hour. The reaction mixture was concentrated, taken up in $H_2O$, washed with ether, followed by saturated sodium chloride, then brought to a pH of 1 with 10% HCl aqueous solution, and extracted into ether. The ether layer was washed with saturated sodium chloride, dried over magnesium sulfate and filtered. The volatiles were removed followed by distillation under high vacuum to give 14.1 g (82%) of a low melting solid, bp=45° C. at 0.10 mm of Hg; mp approximately 25° C.

d. 4,4,4-Trifluorobutanol 36.0 g (255 mM) of the carboxylic acid prepared in Example 45c were added dropwise to a stirred suspension of 11.6 g (306 mM) of lithium aluminum hydride in 300 ml of $Et_2O$ at −78° C. After the addition was completed, the reaction mixture was allowed to warm to rt and stirred an additional 18 hours. After being cooled to 0° C., the reaction mixture was quenched with solid sodium sulfate decahydrate. The reaction mixture was filtered and the solids were collected and washed with $Et_2O$. The combined organic material including filtrate and washes was concentrated to leave 43.6 g of the desired alcohol as a colorless liquid.

e. 1-Bromo-4,4,4-trifluorobutane 5.23 ml (102 mM) of bromine were added dropwise to a stirred solution of 26.7 g (102 mM) of triphenylphosphine in 170 ml of methylene chloride. A precipitate formed. 10.8 g (85 mM) of the alcohol prepared in Example 45d were added dropwise to the resulting stirred suspension cooled to 0° C. The resulting solution was stirred at 0° C. for 2 hours. 0.69 ml of MeOH were added followed by about 125 ml of pentane, whereupon a precipitate formed. The resulting mixture was refluxed for 30 minutes, then cooled and filtered. The filtrate was concentrated carefully and the residue distilled to give 7.22 g of the desired bromo compound as a colorless liquid; bp=55° C. at 100 mm of Hg.

f. 4-Chloro-6-methyl-1-(4,4,4-trifluoro-n-butyl)-1H-pyrazolo[3,4-b]pyridine-5-carboxylic acid ethyl ester The title compound was prepared according to Example 43c using the pyrazolopyridine of Example 43b and the bromotrifluorobutane of Example 45b affording a 68% yield of the product as a clear oil; tlc, $R_f=0.6$, silica gel, EtOAc:hexane (1:3).

g. 4-Amino-6-methyl-1-(4,4,4-trifluoro-n-butyl)-1H-pyrazolo[3,4-b]pyridine-5-carboxylic acid ethyl ester The title compound was prepared according to Example 44e using the product of Example 45f. The amino ester was obtained as a clear oil; tlc, $R_f=0.25$, silica gel, EtOAc:hexane (1:3).

h. 4-Amino-6-methyl-1-(4,4,4-trifluoro-n-butyl)-1H-pyrazolo[3,4-b]pyridine-5-carboxylic acid The title compound was prepared according to Example 44f using the amino ester of Example 45g with the exception that heating was done for 5 hours at 45°

C. The title acid was obtained as a white solid in 58% yield.

i.
4-Amino-6-methyl-1-(4,4,4-trifluoro-n-butyl)-1H-pyrazolo[3,4-b]pyridine-5-carboxylic acid allyl ester The title compound was prepared according to the procedure of Example 43f using the product of Example 45h. The title allyl ester was obtained as a white solid; mp=85°-87° C.; tlc, $R_f$=0.2, silica gel, EtOAc:-hexane (1:3).

Elemental Analysis Calculated for $C_{15}H_{17}N_4O_2F_3$: C, 52.77; H, 5.02; N, 16.41 Found: C, 52.58; H, 5.25; N, 16.48

EXAMPLE 46 a. 5,5,5-Trifluorovaleronitrile

To a stirring solution of 6.40 g (50.3 mM) 4,4,4-trifluorobutanol, prepared in Example 45d, and 7.71 ml (55.3 mM) triethylamine in 1.50 ml Et$_2$O at 0° C. under N$_2$, was added 4.28 ml (55.3 mM) methanesulfonyl chloride dropwise. A white precipitate formed and was stirred 60 minutes at 0° C. An equal volume of pentane was added and the reaction mixture was filtered through celite, followed by concentration on a rotary evaporator without heat. The crude mesylate was mixed with 8.19 g (126 mM) KCN and catalytic KI in 150 ml dimethysulfoxide at rt. The reaction mixture was then heated to 80° C. for 3 hours, turning deep orange and gelling. After cooling, the orange gel was poured into 100 ml of stirring H$_2$O, extracted into Et$_2$O, washed with saturated NaCl, dried over MgSO$_4$, filtered and volatiles distilled. The crude liquid residue was 5.12 g (75%).

b. 5,5,5-Trifluoropentanoic acid

The title compound was prepared by adding 50 ml concentrated H$_2$SO$_4$ to 50 ml distilled H$_2$O, cooling to 50° C., followed by dropwise addition of 6.85 g (50.3 mM) of the product of Example 46a. The reaction mixture was heated under reflux 24 hours, cooled, poured into 120 ml ice water, basified with solid anhydrous Na$_2$CO$_3$, washed with Et$_2$O, acidified with 10% HCl, extracted into Et$_2$O, dried over MgSO$_4$, filtered and the volatiles were distilled yielding 3.67 g (47%) of a colorless liquid.

c. 5,5,5-Trifluoropentanol 3.67 g (23.6 mM) of the product of Example 46b in 5 ml Et$_2$O were slowly added via cannula to a mechanically stirring suspension of 0.99 g (26.0 mM) lithium aluminum hydride in 25 ml anhydrous Et$_2$O at −78° C. After the addition was completed, the reaction was warmed to rt, stirred 24 hours and subsequently quenched at 0° C. with solid Na$_2$SO$_4$.10H$_2$O until white. The white precipitate was filtered and washed with Et$_2$O. The volatiles were distilled leaving a colorless liquid, which was distilled yielding 2.45 g (73%) of a colorless liquid, bp=70° C. at 40 mm of Hg.

d. 1-Bromo-5,5,5-trifluoropentane

To a rt solution of 5.46 g (20.8 mM) triphenylphosphine in 35 ml CH$_2$Cl$_2$ was added via dropping funnel 1.07 ml (20.8 mM) bromine. The PPh$_3$Br$_2$ suspension was cooled to 0° C., followed by dropwise addition of 2.45 g (17.35 mM) of the product of Example 46c. After stirring 2 hours, 0.13 ml (3.86 mM) MeOH was added to discharge excess PPh$_3$Br$_2$. An equal volume of pentane was added to precipitate triphenylphosphine oxide. The reaction mixture was heated under reflux for 30 minutes, filtered and distilled to yield 2.62 g (74%) of a colorless liquid, bp=70° C. at 50 mm of Hg.

e.
4-Chloro-6-methyl-1-(5,5,5-trifluoro-n-pentyl)-1H-pyrazolo[3,4-b]pyridine-5-carboxylic acid ethyl ester The title compound was prepared according to Example 43c using the pyrazolopyridine of Example 43b and the product of Example 46d giving a 70% yield of the title product as a clear oil; tlc, $R_f$=0.6, silica gel, EtOAc:hexane (1:3).

f.
4-Amino-6-methyl-1-(5,5,5-trifluoro-n-pentyl)-1H-pyrazolo[3,4-b]pyridine-5-carboxylic acid ethyl ester The title compound was prepared according to the procedure of Example 43d using the product of Example 46e except that the reaction time was extended to 12 hours. The amino ester was obtained in a 94% yield as a clear oil; tlc, $R_f$=0.25, silica gel, EtOAc:hexane (1:3).

g.
4-Amino-6-methyl-1-(5,5,5-trifluoro-n-pentyl)-1H-pyrazolo[3,4-b]pyridine-5-carboxylic acid The title compound was prepared according to Example 45e using the amino ester of Example 46f. The title acid was obtained as a white solid.

h.
4-Amino-6-methyl-1-(5,5,5-trifluoro-n-pentyl)-1H-pyrazolo[3,4-b]pyridine-5-carboxylic acid allyl ester The title compound was prepared according to Example 43f using the product of Example 46 g. The title ester was obtained as a white solid in 69% yield, mp=64°-65° C.; tlc, $R_f$=0.25, silica gel, EtOAc:hexane (1:3).

Elemental Analysis Calculated for $C_{16}H_{19}N_4O_2F_3$: C, 54.06; H, 5.39; N, 15.76 Found: C, 53.44; H, 5.49; N, 16.25

EXAMPLE 47

4-Amino-6-methyl-1-pentyl-1H-pyrazolo[3,4-b]pyridine-5-carboxylic acid phenyl ester The product of Example 2a was prepared from 1.5 g (5.7 mM) of the corresponding amino acid as in Example 2a and was then suspended in 15 ml of CH$_2$Cl$_2$. To the stirred ice bath cooled suspension was added 2.7 g (28.7 mM) of phenol and the resulting mixture was stirred at rt for 2 hours. After the removal of CH$_2$Cl$_2$, the residue was basified with a saturated solution of Na$_2$CO$_3$, the product was extracted with EtOAc, and the EtOAc layer was washed successively with aqueous NaOH solution and water. After drying over MgSO$_4$, the organic layer was filtered and concentrated to leave 1.64 g of phenyl ester as white solid which was dissolved in Et$_2$O and was converted to the hydrochloride salt as a white solid by adding HCl in Et$_2$O; mp=128°-129° C.

Elemental Analysis Calculated for $C_{19}H_{22}N_4O_2$.HCl: C, 60.87; H, 6.18; N, 14.94; Cl, 9.46 Found: C, 60.73; H, 6.22; N, 14.88; Cl, 9.60

What is claimed is:

1. A pyrazolo[3,4-b]pyridine of the formula:

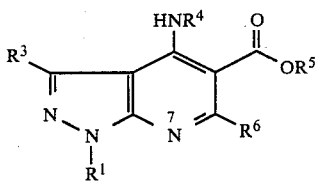

wherein
R¹ is a straight or branched chain alkyl of 1 to 10 carbons, cycloalkyl of 3 to 8 carbons, cycloalkylalkyl of 4 to 12 carbons, alkenyl or alkynyl of 3 to 10 carbons, arylalkyl of 7 to 12 carbons; straight or branched chain alkyl of 1 to 10 carbons into the backbone of which is inserted an oxygen, sulfur, sulfinyl or sulfonyl divalent moiety, or straight or branched chain alkyl of 1 to 10 carbons substituted by a hydroxy, amino, 1 to 6 carbon alkylamino, 2 to 12 carbon dialkylamino, cyano, oxo, ketal, hemiketal, acetal or hemiacetal group, wherein the alkyl group or groups of the ketal, hemiketal, acetal or hemiacetal each are of 1 to 6 carbons, or by one or more of chloro, bromo, iodo or fluoro groups;

R³ is hydrogen or straight or branched chain alkyl of 1 to 6 carbons;

R⁴ is hydrogen, straight or branched chain alkyl of 1 to 10 carbons or straight or branched chain alkyl of 1 to 10 carbons substituted by a hydroxy or oxo group;

R⁵ is straight or branched chain alkenyl of 3 to 7 carbons, straight or branched chain alkynyl of 3 to 7 carbons, hydroxy(straight or branched chain)alkyl of 1 to 7 carbons, cycloalkyl of 3 to 7 carbons, cycloalkylalkyl of 4 to 10 carbons, alkoxy(straight or branched chain)alkyl of 2 to 10 carbons, straight or branched chain alkyl of 2 to 7 carbons substituted by one or more halogen atoms, straight or branched chain alkenyl of 3 to 7 carbons substituted by one or more halogen atoms, aryl(straight or branched chain)alkyl of 6 to 10 carbons in the aryl portion and 1 to 7 carbons in the alkyl portion; aryl-(straight or branched chain)alkenyl of 6 to 10 carbons in the aryl portion and 3 to 7 carbons in the alkenyl portion, or phenyl; and R⁶ is hydrogen or straight or branched chain alkyl of 1 to 8 carbons, or an N-oxide at the 7-position of the pyrazolo [3,4,-b]-pyridine ring system, or a pharmaceutically acceptable acid-addition salt thereof.

2. A compound as claimed in claim 1 wherein
R¹ is (3-7C) alkyl, cycloalkylalkyl of not more than 7 carbons, (3-7C) alkenyl, (3-7C) alkynyl or phenyl-(1-3C)alkyl;
R³ is hydrogen or methyl;
R⁴ is hydrogen, (1-6C) alkyl, (1-6C) hydroxy-substituted alkyl, (1-6C) aldehydo-substituted alkyl or (1-6C) keto-substituted alkyl;
R⁵ is (3-7C) alkenyl, (3-7C) alkynyl, (1-7C) hydroxy alkyl, (3-7C) cycloalkyl, (4-10C) cycloalkylalkyl, (2-10C) alkoxyalkyl, (2-7C) haloalkyl, (3-7C) haloalkenyl, (6-10C) arylalkyl or (6-10C) arylalkenyl; and
R⁶ is methyl,
or an N-oxide at the 7-position of the pyrazolo[3,4-b]pyridine ring system, or a pharmaceutically-acceptable acid-addition salt thereof.

3. A compound as claimed in claim 1 which is the free base at the 7-position.

4. A compound as claimed in claim 1 wherein
R¹ is (4-5C) alkyl, cycloalkylalkyl of 5 carbons, (3-7C) alkenyl, (3-7C) alkynyl or phenyl-(1-3C)alkyl, or a (3-7C) alkyl into which is inserted a divalent moiety selected from oxygen, sulfur, sulfinyl and sulfonyl, or a (3-7C) alkyl bearing a hydroxy, cyano, oxo, ketal or trifluoromethyl substituent;
R³ is hydrogen;
R⁴ is hydrogen;
R⁵ is (3-7C) alkenyl, (3-7C) alkynyl, cycloalkylalkyl or alkoxyalkyl of not more than 7 carbons in total, halo-(3-7C)alkenyl, phenyl-(1-3C)alkyl, phenyl(3-7C)alkenyl or phenyl; and
R⁶ is hydrogen or methyl;
or a pharmaceutically-acceptable acid-addition salt thereof.

5. A compound as claimed in claim 1 which is
4-amino-6-methyl-1-pentyl-1H-pyrazolo[3,4-b]-pyridine-5-carboxylic acid cyclopropylmethyl ester,
4-amino-1-(4-cyanobutyl)-6-methyl-1H-pyrazolo[3,4-b]pyridine-5-carboxylic acid allyl ester or
4-amino-6-methyl-1-(4-oxo-n-pentyl)-1H-pyrazolo[3,4-b]pyridine-5-carboxylic acid allyl ester, or a pharmaceutically-acceptable acid-addition salt thereof.

6. A pyrazolo[3,4-b]pyridine of the formula:

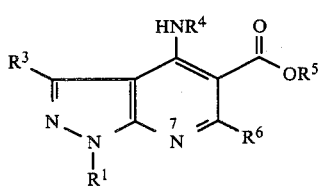

which is 4-amino-6-methyl-1-(4-pentynyl)-1H-pyrazolo[3,4-b]pyridine-5-carboxylic acid allyl ester or a pharmaceutically-acceptable acid-addition salt thereof.

7. A pharmaceutical composition comprising a central-nervoussystem depressing amount of at least one compound of the formula stated in claim 1, or an N-oxide at the 7-position of the pyrazolo[3,4-b]pyridine ring system, or a pharmaceutically-acceptable acid-addition salt thereof, and a pharmaceutically-acceptable diluent or carrier.

8. A method of suppressing central nervous system activity in mammals comprising administering to the mammal a pharmaceutically effective amount of a composition of claim 7.

9. A method for the treatment of anxiety in humans comprising administering a pharmaceutically effective amount of the pharmaceutical composition of claim 7 to a human in need thereof.

* * * * *

UNITED STATES PATENT AND TRADEMARK OFFICE
CERTIFICATE OF CORRECTION

PATENT NO. : 4,552,883
DATED : November 12, 1985
INVENTOR(S) : Thomas M. Bare

It is certified that error appears in the above—identified patent and that said Letters Patent is hereby corrected as shown below:

Column 7, line 2: after "pyrazolopyridine" insert --ring--.

Column 11, line 61: after "R" delete "32" and insert an equal sign (=).

Column 23, line 12: "silical" should be "silica".

Column 27, line 67: "$HN_3$" should be "$NH_3$".

Column 29, line 49: "be" should be "by".

Column 33, line 31: "following" should be "followed".

Signed and Sealed this

Sixteenth Day of September 1986

[SEAL]

Attest:

DONALD J. QUIGG

Attesting Officer     Commissioner of Patents and Trademarks